US012594254B2

(12) United States Patent
Greene et al.

(10) Patent No.: US 12,594,254 B2
(45) Date of Patent: Apr. 7, 2026

(54) INTRANASAL ADMINISTRATION OF N-ACETYLCYSTEINE AND USES THEREOF

(71) Applicant: Neuronasal, Inc., Wexford, PA (US)

(72) Inventors: Douglas A. Greene, Basking Ridge, NJ (US); Thomas I. Bradshaw, Wynnewood, PA (US)

(73) Assignee: Neuronasal, Inc., Wexford, PA (US)

( * ) Notice: Subject to any disclaimer, the term of this patent is extended or adjusted under 35 U.S.C. 154(b) by 0 days.

(21) Appl. No.: 18/855,563

(22) PCT Filed: Feb. 7, 2023

(86) PCT No.: PCT/US2023/012538

§ 371 (c)(1),
(2) Date: Oct. 9, 2024

(87) PCT Pub. No.: WO2023/150392

PCT Pub. Date: Aug. 10, 2023

(65) Prior Publication Data

US 2025/0221951 A1 Jul. 10, 2025

Related U.S. Application Data

(60) Provisional application No. 63/307,260, filed on Feb. 7, 2022.

(51) Int. Cl.

| | |
|---|---|
| ***A61K 31/198*** | (2006.01) |
| ***A61K 9/00*** | (2006.01) |
| ***A61K 38/06*** | (2006.01) |
| ***A61K 45/06*** | (2006.01) |

(52) U.S. Cl.
CPC .......... *A61K 31/198* (2013.01); *A61K 9/0043* (2013.01); *A61K 38/063* (2013.01); *A61K 45/06* (2013.01)

(58) Field of Classification Search
CPC .................................................... A61K 31/198
See application file for complete search history.

(56) References Cited

U.S. PATENT DOCUMENTS

| | | | | |
|---|---|---|---|---|
| 12,090,130 | B2 * | 9/2024 | Greene | A61P 25/00 |
| 2013/0184316 | A1 * | 7/2013 | Hornstein | A61K 31/44 600/301 |
| 2018/0344678 | A1 * | 12/2018 | Ratan | A61K 9/0043 |

* cited by examiner

*Primary Examiner* — Rei Tsang Shiao
(74) *Attorney, Agent, or Firm* — FBT GIBBONS LLP

(57) ABSTRACT

The present disclosure describes methods comprising administering N-acetylcysteine (NAC) or a pharmaceutically-acceptable salt or congener thereof. The disclosed methods can be used to treat a brain disorder.

43 Claims, 4 Drawing Sheets

INTRANASAL ADMINISTRATION OF N-ACETYLCYSTEINE AND USES THEREOF

CROSS-REFERENCE

This application claims the benefit of U.S. Provisional Application No. 63/307,260 filed Feb. 7, 2022, which is incorporated herein by reference in its entirety.

BACKGROUND

N-acetylcysteine (NAC) acts as an antioxidant, brain glutathione (GSH) precursor, and inhibitor of neuro-excitotoxicity and neuro-inflammation.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Figure 1:
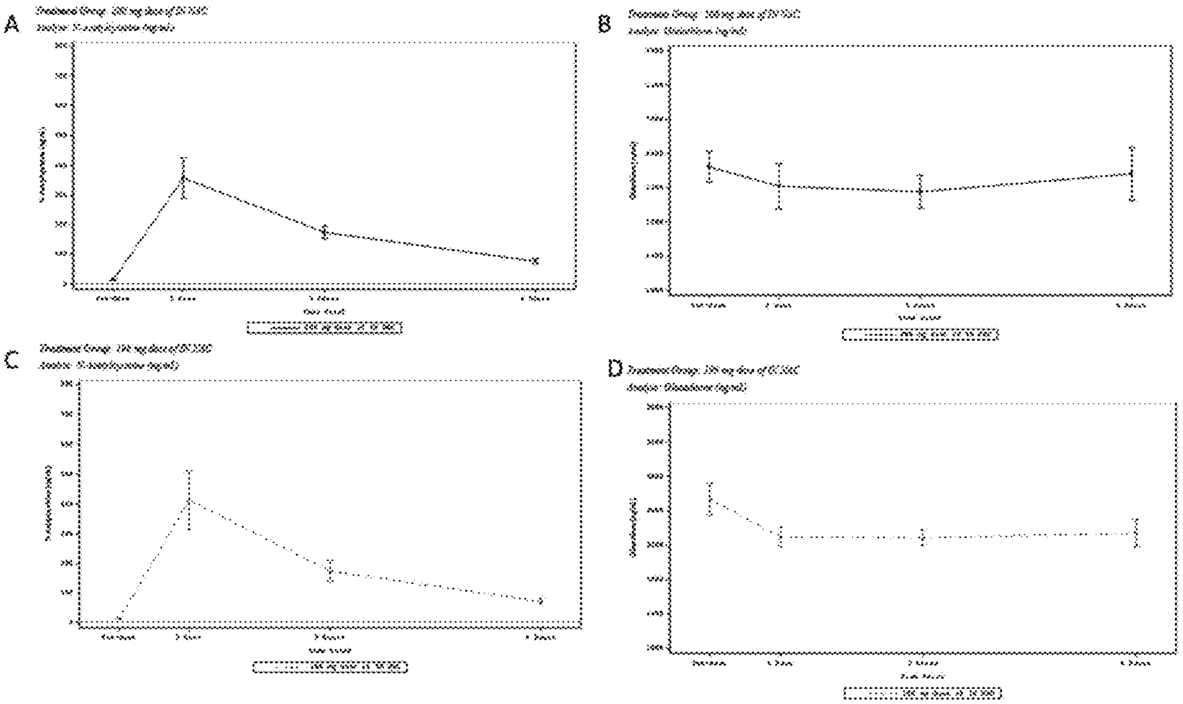
FIG. 1A shows linear N-acetylcysteine (NAC) mean (±SE) blood pharmacokinetic (PK) data over time following intranasal (IN) administration of 200 mg NAC delivered with a Teleflex Mucosal Atomisation Device (MAD).
FIG. 1B shows linear Glutathione (GSH) mean (±SE) blood PK data over time following 200 mg IN NAC delivered with a Teleflex MAD device.
FIG. 1C shows linear NAC mean (±SE) blood PK data over time following 196 mg IN NAC delivered with a APTAR 5 mL CPS Syringe.
FIG. 1D shows linear GSH mean (±SE) blood PK data over time following 196 mg IN NAC delivered with a APTAR 5 mL CPS Syringe.

NAC is a small molecule precursor of L-cysteine that results in glutathione elevation biosynthesis. NAC is a powerful antioxidant that acts directly as a scavenger of free radicals, for example, oxygen free radicals. NAC has a range of pleotropic, salutary effects on acute and chronic central nervous system (CNS) disorders through a variety of biochemical and pharmacological mechanisms of action, including quenching of reactive oxygen species (ROS), chelation of oxidative reactive metal ions, anti-inflammation, and neuromodulation via the cystine-glutamate antiporter. NAC can also increase the concentration and bioavailability of the endogenous antioxidant glutathione (GSH), anti-excitotoxic activity, and heavy metal-chelating activity.

NAC, NAC congeners, and NAC derivatives can exhibit beneficial effects in acute and chronic, focal, and diffuse forms of brain injury and brain disorders, including traumatic brain injury (TBI) in humans and pre-clinical animal models. The pharmacological properties of NAC derive from NAC's metabolic conversion to cysteine and reduced GSH, which provide protection against damaging neuro-excitotoxicity, oxidative damage, and inflammation. NAC provides protection against neuro-excitotoxicity by generating cysteine, a substrate for the cysteine-glutamate transporter. However, NAC has poor systemic availability and poor oral bioavailability due to high first-pass hepatic metabolism and uncertain transfer across the blood-brain barrier (BBB). Tolerable dose-volumes of readily available aqueous solutions of NAC often cannot achieve sufficient levels of measured brain penetrability and/or bioactivity.

Provided herein are methods of administering NAC or GSH to the central nervous system (CNS) using intranasal (IN) nose-to-brain direct delivery.

In some embodiments, the disclosure provides a method of treating a brain disorder in a brain of a subject in need thereof, the method comprising intranasally administering to a nose of the subject a dose of NAC or a congener thereof and a therapeutic agent. In some embodiments, co-administration of IN NAC with a therapeutic agent, and the subject is not substantially systemically exposed to the NAC or the congener thereof upon the IN administration. In some embodiments, co-administration of IN NAC with a therapeutic agent can provide a therapeutically-effective amount of the NAC, or the congener thereof, to the brain from the nose, wherein substantially all of the NAC, or the congener thereof, enters the brain without crossing a blood brain barrier of the subject. In some embodiments, co-administration of IN NAC with a therapeutic agent can deliver the NAC or the therapeutic agent to the brain from the nose, wherein the NAC or the therapeutic agent crosses an olfactory epithelium of the subject, and then after crossing the olfactory epithelium the NAC or the therapeutic agent enters the olfactory nerve of the subject, and then after crossing the olfactory nerve, the NAC or the therapeutic agent enters the brain. In some embodiments, co-administration of IN NAC with a therapeutic agent can deliver the NAC or the therapeutic agent to the brain from the nose, wherein the NAC or the therapeutic agent crosses an olfactory epithelium of the subject, and then after crossing the olfactory epithelium the NAC or the therapeutic agent enters the olfactory nerve of the subject, and then after crossing the olfactory nerve, the NAC or the therapeutic agent enters the cerebral spinal fluid of the subject, then enters the brain. In some embodiments, co-administration of IN NAC with a therapeutic agent can deliver the NAC or the therapeutic agent to the brain from the nose, wherein the NAC or the therapeutic agent crosses a respiratory epithelium of the subject, then after crossing the respiratory epithelium, the NAC or the therapeutic agent crosses a trigeminal nerve of the subject, and then after crossing the trigeminal nerve, then enters the brain.

In some embodiments, co-administration of IN NAC with a therapeutic agent can increase the delivery efficiency of the therapeutic agent. In some embodiments, co-administration of IN NAC with a therapeutic agent can deliver the therapeutic agent directly from the nose to the brain. In some embodiments, co-administration of IN NAC with a therapeutic agent can delivery the therapeutic agent to the brain without crossing a blood-brain barrier of the subject.

Compounds of the Disclosure

NAC is a glutathione prodrug that is used to treat acetaminophen-induced liver failure and to loosen thick mucus individuals with cystic fibrosis or chronic obstructive pulmonary disease. NAC can be taken intravenously, by mouth, or inhaled as a mist. Common side effects of NAC include nausea and vomiting when NAC is administered orally. NAC can also cause skin redness and itching and a non-immune type of anaphylaxis. NAC has multiple putative targets of action, and NAC has poor penetration into the CNS. NAC has been reported to cause nausea and vomiting, induce bronchospasm, slow blood clotting, and induce neurotoxicity in a dose-dependent manner. These issues can be problematic for patients with hemorrhagic stroke.

The present disclosure describes the co-administration of at least one compound or a pharmaceutically-acceptable salt thereof and a therapeutic agent to treat a condition. In some embodiments, the compound is N-acetylcysteine NAC, NAC amide (NACA), NAC derivative, NAC metabolite, NAC congener, or NAC dendrimer (D-NAC), or a pharmaceutically-acceptable salt thereof. In some embodiments, the compound is a NAC prodrug or a pharmaceutically-acceptable slat thereof. In some embodiments, the compounds is NAC. In some embodiments, the compound is a NAC derivative. In some embodiments, the NAC derivative is GSH.

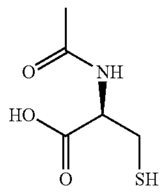

N-Acetylcysteine

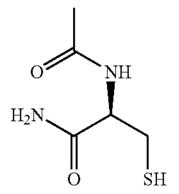

N-Acetylcysteine amide

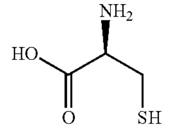

Cysteine

In some embodiments, the compound is a NAC dendrimer. Dendrimer-NAC (D-NAC) is a dendrimer conjugate where NAC is covalently bound to the surface of a dendrimer by disulfide linkages. In some embodiments, D-NAC comprises a polyamidoamine (PAMAM) hydroxyl dendrimer. In some embodiments, D-NAC comprises a polyglycerol sulfate dendrimer. In some embodiments, D-NAC comprises a polyamine dendrimer. In some embodiments, D-NAC comprises a polyamide dendrimer. In some embodiments, D-NAC comprises a linker. In some embodiments, GABA comprises a gamma-aminobutyric acid (GABA) linker. In some embodiments, D-NAC comprises a succinimidyl 3-(2-pyridyldithio)propionate (SPDP) linker.

In some embodiments, D-NAC has the formula:

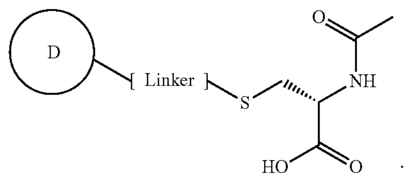

.

In some embodiments, D-NAC has the formula:

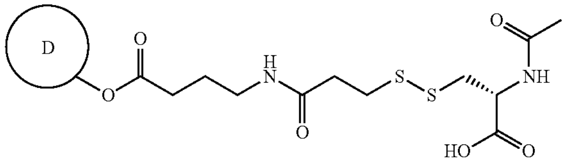

.

Purity of Compounds of the Disclosure

Any compound of the disclosure (e.g., NAC, a NAC congener, or a NAC derivative) can be purified. A compound of the disclosure (e.g., NAC, a NAC congener, or a NAC derivative) can be designated a drug. A compound as described herein can be least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

Intranasal Nose-to-Brain Delivery

As demonstrated herein, the nasal cavity is suitable for drug delivery as the nasal mucosa provides for efficient absorption of pharmaceutically active molecules. The roof of the nasal cavity is located in close vicinity to the brain and harbors nerves that project to the brain. Therefore, a useful strategy to bypass the blood-brain barrier is the delivery of drugs from the nose to the brain (referred to herein as "nose-to-brain" or "N2B"). The nose-to-brain drug administration route delivers substances to the brain via the olfactory and/or trigeminal nerve. Nose-to-brain delivery can be used to deliver small molecule drugs, peptides or proteins, stem cells, viruses, and nucleotides.

Thus, pharmaceutically active small molecules (e.g., NAC or GSH) or biologic molecules (e.g., peptides) deposited on the nasal mucosa can traverse directly to the CNS by one or more multiple alternative or complementary pathways. The effectiveness of CNS delivery can depend on the anatomical site of deposition, molecular characteristics of the drug or biologic, the formulation, and the animal species under consideration. Nose-to-brain delivery can be minimally invasive with adequate patient compliance.

Disclosed herein is the use of intranasal administration of NAC, NACA, NAC derivative, NAC metabolite, NAC congener, or D-NAC to optimize nose-to-brain delivery of a therapeutic agent to one or more regions of the brain that are susceptible to, or have undergone, injury from an acute or chronic brain disorder. In some embodiments, co-administration of intranasal nose-to-brain delivery of NAC, NACA, NAC derivative, NAC metabolite, NAC congener, or D-NAC with a therapeutic agent can prevent, lessen the likelihood of developing, delay, or ameliorate a brain injury. In some embodiments, co-administration of intranasal nose-to-brain delivery of NAC, NACA, NAC derivative, NAC metabolite, NAC congener, or D-NAC with a therapeutic agent can improve or prevent signs, symptoms, or disabilities associated with brain injury. In some embodiments, co-administration of intranasal nose-to-brain delivery of NAC, NACA, NAC derivative, NAC metabolite, NAC congener, or D-NAC with a therapeutic agent can improve or prevent signs or symptoms of treatment-resistant depression. In some embodiments, the NAC congener is GSH.

Also disclosed herein are delivery devices and formulations that promote direct transfer of NAC, NACA, NAC derivative, NAC metabolite, NAC congener, or D-NAC and a therapeutic agent to the brain while avoiding systemic circulation that eliminates the active substances, thereby avoiding systemic disposition. In some embodiments, the delivery devices and formulations of the disclosure promote direct transfer of NAC. In some embodiments, the delivery devices and formulations of the disclosure promote direct transfer of GSH. The intranasal NAC or GSH formulations of the disclosure are designed to facilitate entry of NAC, NACA, NAC derivative, NAC metabolite, NAC congener, or D-NAC or a therapeutic agent into specific portals for anatomical pathways of nose-to-brain drug transfer. In some embodiments, co-administration of intranasal NAC or GSH formulations and a therapeutic agent of the disclosure maximizes entry of NAC, NACA, NAC derivative, NAC metabolite, NAC congener, or D-NAC or a therapeutic agent via nose-to-brain drug transfer by allowing higher concentrations of NAC, GSH, or the therapeutic agent to be delivered to the nasal mucosal surface. In some embodiments, co-administration of intranasal NAC or GSH formulations and a therapeutic agent of the disclosure maximizes entry of NAC, NACA, NAC derivative, NAC metabolite, NAC congener (e.g., GSH), or D-NAC or the therapeutic agent via nose-to-brain drug transfer by minimizing local loss of nasally delivered NAC or GSH by mucociliary clearance and elimination via systemic circulation. In some embodiments, co-administration of intranasal NAC or GSH formulations and a therapeutic agent of the disclosure maximizes entry of NAC, NACA, NAC derivative, NAC metabolite, NAC congener (e.g., GSH), or D-NAC or the therapeutic agent via nose-to-brain drug transfer by increasing delivery through the mucus barrier that coats the interior of the nasal cavity, and the delivery mechanism benefits from NAC's and GSH's intrinsic mucolytic characteristics. In some embodiments, co-administration of intranasal NAC or GSH formulations and a therapeutic agent of the disclosure maximize entry of NAC, NACA, NAC derivative, NAC metabolite, NAC congener (e.g., GSH), or D-NAC or the therapeutic agent via nose-to-brain drug transfer by enhancing transport through or between nasal epithelial cells or increasing uptake into the space surrounding nerve cells that project into the brain.

In some embodiments, after administration, a compound or therapeutic agent of the disclosure can be transported through the olfactory pathway. In some embodiments, after administration, a compound or therapeutic agent of the disclosure can be transported through the trigeminal pathway. In some embodiments, the compound or therapeutic agent of the disclosure does not pass through the blood brain barrier. In some embodiments, the subject receiving the compound or therapeutic agent is not substantially systemically exposed to the compound. In some embodiments, a portion of the compound or therapeutic agent can be transported through the olfactory pathway, and another portion of the compound or therapeutic agent can be transported through the trigeminal pathway. In some embodiments, about 1% to about 99% of the compound or therapeutic agent can be transported through the olfactory pathway, and about 99% to about 1% of the compound or therapeutic agent can be transported through the trigeminal pathway. In some embodiments, about 5% to about 95% of the compound or therapeutic agent can be transported through the olfactory pathway, and about 95% to about 5% of the compound or therapeutic agent can be transported through the trigeminal pathway. In some embodiments, about 10% to about 90% of the compound or therapeutic agent can be transported through the olfactory pathway, and about 90% to about 10% of the compound or therapeutic agent can be transported through the trigeminal pathway. In some embodiments, about 15% to about 85% of the compound or therapeutic agent can be transported through the olfactory pathway, and about 85% to about 15% of the compound or therapeutic agent can be transported through the trigeminal pathway. In some embodiments, about 20% to about 80% of the compound or therapeutic agent can be transported through the olfactory pathway, and about 80% to about 20% of the compound or therapeutic agent can be transported through the trigeminal pathway. In some embodiments, about 25% to about 75% of the compound or therapeutic agent can be transported through the olfactory pathway, and about 75% to about 25% of the compound or therapeutic agent can be transported through the trigeminal pathway. In some embodiments, about 30% to about 70% of the compound or therapeutic agent can be transported through the olfactory pathway, and about 70% to about 30% of the compound or therapeutic agent can be transported through the trigeminal pathway. In some embodiments, about 35% to about 65% of the compound or therapeutic agent can be transported through the olfactory pathway, and about 65% to about 35% of the compound or therapeutic agent can be transported through the trigeminal pathway. In some embodiments, about 40% to about 60% of the compound or therapeutic agent can be transported through the olfactory pathway, and about 60% to about 40% of the compound or therapeutic agent can be transported through the trigeminal pathway. In some embodiments, about 55% to about 45% of the compound or therapeutic agent can be transported through the olfactory pathway, and about 45% to about 55% of the compound or therapeutic agent can be transported through the trigeminal pathway. In some embodiments, about 50% of the compound or therapeutic agent can be transported through the olfactory pathway, and about 50% of the compound or therapeutic agent can be transported through the trigeminal pathway.

In some embodiments, a compound or therapeutic agent can be transported through olfactory pathway and trigeminal pathway at an olfactory:trigeminal ratio of about 1:99, about 2:98, about 3:97, about 4:96, about 5:95, about 6:94, about 7:93, about 8:92, about 9:91, about 10:90, about 11:89, about 12:88, about 13:87, about 14:86, about 15:85, about 16:84, about 17:83, about 18:82, about 19:81, about 20:80, about 21:79, about 22:78, about 23:77, about 24:76, about 25:75, about 26:74, about 27:73, about 28:72, about 29:71, about 30:70, about 31:69, about 32:68, about 33:67, about 34:66, about 35:65, about 36:64, about 37:63, about 38:62, about 39:61, about 40:60, about 41:59, about 42:58, about 43:57, about 44:56, about 45:55, about 46:54, about 47:53, about 48:52, about 49:51, about 50:50, about 51:49, about 52:48, about 53:47, about 54:46, about 55:45, about 56:44, about 57:43, about 58:42, about 59:41, about 60:40, about 61:39, about 62:38, about 63:37, about 64:36, about 65:35, about 66:34, about 67:33, about 68:32, about 69:31, about 70:30, about 71:29, about 72:28, about 73:27, about 74:26, about 75:25, about 76:24, about 77:23, about 78:22, about 69:21, about 80:20, about 81:19, about 82:18, about 83:17, about 84:16, about 85:15, about 86:14, about 87:13, about 88:12, about 89:11, about 90:10, about 91:9, about 92:8, about 93:7, about 94:6, about 95:5, about 96:4, about 97:3, about 98:2, or about 99:1.

In some embodiments, a compound of the disclosure (e.g., NAC, NACA, NAC derivative, NAC metabolite, NAC congener, or D-NAC) or therapeutic agent does not enter the systemic circulation. Thus, in some embodiments, the subject is not substantially systemically exposed to the compound or therapeutic agent of the disclosure. In some embodiments, the compound or therapeutic agent of the disclosure does not cross the blood brain barrier. In some embodiments, a compound or therapeutic agent of the disclosure is administered in the nasal cavity, then crosses the respiratory epithelium; then after crossing the respiratory epithelium, the compound or therapeutic agent crosses the trigeminal nerve without entering the systemic circulation; then after crossing the trigeminal nerve, the compound or therapeutic agent enters the brain without entering the systemic circulation or crossing the blood-brain barrier.

In some embodiments, although the subject is not substantially systemically exposed to a compound or therapeutic agent of the disclosure, a portion of administered amount of the compound or therapeutic agent can enter systemic circulation. In some embodiments, a dose of a compound or therapeutic agent entering the respiratory epithelium partially enters the systemic circulation. In some embodiments, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% or more of the compound or therapeutic agent enters the systemic circulation. In some embodiments, less than about 50% of the compound or therapeutic agent enters the systemic circulation. In some embodiments, less than about 40% of the compound or therapeutic agent enters the systemic circulation. In some embodiments, less than about 30% of the compound or therapeutic agent enters the systemic circulation. In some embodiments, less than about 20% of the compound or therapeutic agent enters the systemic circulation. In some embodiments, less than about 10% of the compound or therapeutic agent enters the systemic circulation. In some embodiments, less than about 5% of the compound or therapeutic agent enters the systemic circulation. In some embodiments, less than about 1% of the compound or therapeutic agent enters the systemic circulation.

In some embodiments, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% or more of the compound or therapeutic agent crosses the blood brain barrier. In some embodiments, less than about 50% of the compound or therapeutic agent crosses the blood brain barrier. In some embodiments, less than about 40% of the compound or therapeutic agent crosses the blood brain barrier. In some embodiments, less than about 30% of the compound or therapeutic agent crosses the blood brain barrier. In some embodiments, less than about 20% of the compound or therapeutic agent crosses the blood brain barrier. In some embodiments, less than about 10% of the compound or therapeutic agent crosses the blood brain barrier. In some embodiments, less than about 5% of the compound or therapeutic agent crosses the blood brain barrier. In some embodiments, less than about 1% of the compound or therapeutic agent crosses the blood brain barrier.

Therapeutic Methods

The present disclosure describes the use of a compound or therapeutic agent and methods to treat a brain disorder. The disclosure also describes techniques to target NAC, NACA, NAC derivative, NAC metabolite, NAC congener, or D-NAC and a therapeutic agent directly to the CNS while avoiding high first-pass hepatic metabolism and circumventing the blood brain barrier. In some embodiments, the compounds, therapeutic agents, and methods of the disclosure can be used to treat a brain disorder. In some embodiments, the compounds, therapeutic agents, and methods of the disclosure can be used to treat a brain injury. In some embodiments, the brain disorder can be a form of brain damage, for example, brain damage resulting from a traumatic brain injury. In some embodiments, the brain disorder can be a disorder of the nervous system. Structural, biochemical, or electrical abnormalities in the brain, spinal cord, or other nerves can result in a range of symptoms. Examples of symptoms that arise from neurological disorders include paralysis, muscle weakness, poor coordination, loss of sensation, seizures, confusion, pain, and altered levels of consciousness.

The compounds, therapeutic agents, and methods of the disclosure can be used to treat a CNS condition. CNS disorders are a group of neurological disorders that affect the structure or function of the brain or spinal cord, which collectively form the CNS. The disclosure describes compounds, therapeutic agents, and methods to treat a CNS disorder caused by traumatic brain injury, mild traumatic brain injury, concussion, mild concussion, post-concussion syndrome, infections, degeneration (e.g., degenerative spinal disorders), structural defects (e.g., anencephaly, hypospadias, spina *bifida*, microgyria, polymicrogyria, bilateral frontoparietal polymicrogyria, or pachgyria), tumors, autoimmune disorders, or stroke. In some embodiments, the disclosure describes compounds, therapeutic agents, and methods of treating the use of a compound of the disclosure to treat traumatic brain injury. In some embodiments, the disclosure describes the use of a compound of the disclosure and a therapeutic agent to treat mild traumatic brain injury. In some embodiments, the disclosure describes the use of a compound of the disclosure and a therapeutic agent to treat subarachnoid hemorrhage. In some embodiments, the disclosure describes the use of a compound of the disclosure and a therapeutic agent to treat concussion. In some embodiments, the disclosure describes the use of a compound of the disclosure to treat a mild concussion. In some embodiments, the disclosure describes the use of a compound of the disclosure to treat post-concussion syndrome.

In some embodiments, the disclosure describes the use of a compound of the disclosure and a therapeutic agent to treat stroke. Stroke is a medical condition in which poor blood flow to the brain results in cell death. The two main types of strokes are ischemic stroke resulting from a lack of blood flow, and hemorrhagic stroke resulting from bleeding. Signs and symptoms of a stroke include an inability to move or feel on one side of the body, problems understanding or speaking, and a loss of vision to one side. In some embodiments, the disclosure describes the use of a compound of the disclosure and a therapeutic agent to treat hemorrhagic stroke. In some embodiments, the disclosure describes the use of a compound of the disclosure and a therapeutic agent to treat ICH stroke.

In some embodiments, the present disclosure describes the use of a compound of the disclosure and a therapeutic agent for treating brain damage. In some embodiments, the brain damage is due to brain injury resulting from an acute event, such as traumatic brain injury. Brain injury resulting from an acute event is sometimes referred to as primary brain injury. In some embodiments, the disclosure describes the use of a compound of the disclosure and a therapeutic agent to treat traumatic brain injury. In some embodiments, the disclosure describes the use of a compound of the disclosure and a therapeutic agent to treat mild traumatic brain injury. Brain injury resulting from an acute event can be caused by a blow to the head from, e.g., falls, violence, accidents, child abuse, sports injuries, and blast injuries due to explosions. In some embodiments, the present disclosure describes the use of a compound of the disclosure and a therapeutic agent for treating a concussion. In some embodiments, the present disclosure describes the use of a compound of the disclosure and a therapeutic agent for treating a mild concussion.

In some embodiments, a compound of the disclosure and a therapeutic agent is used to treat brain damage due to subsequent secondary brain injury resulting from primary brain injury. A secondary brain injury can include the changes that evolve over a period of hours to days after the primary brain injury. Secondary brain injury includes a cascade of cellular, chemical, tissue, or blood vessel changes in the brain that contribute to further destruction of brain tissue.

In some embodiments, a compound of the disclosure and a therapeutic agent is used to treat a brain injury resulting from exposure to agents that are involved in secondary brain damage or neurodegeneration, such as glutamate, glutamate receptor ligands, hypoxia-mimicking agents, nitric oxide generating agents, apoptosis-inducing agents, steroids, ammonium chloride, toxic compounds, or agents that interfere with ATP production. In some embodiments, a compound of the disclosure and a therapeutic agent is used to treat brain damage due to a chronic challenge such as infection, toxins, and excessive drug use of recreational, over the counter, and/or prescription drugs.

In some embodiments, the compounds, therapeutic agents, and methods of the present disclosure can be used to treat military personnel, for example, soldiers in the battlefield, especially soldiers who have suffered traumatic brain injury and/or secondary brain damage resulting from traumatic brain injury. In some embodiments, the compounds, therapeutic agents, and methods of the disclosure can be used to treat traumatic brain injury and/or secondary brain damage resulting from traumatic brain injury can be treated by administering the compounds of the disclosure and a therapeutic agent to soldiers, for example by supplying the compounds of the disclosure and a therapeutic agent to paramedics and/or the soldiers in the battlefield or under threat/at the site of terrorist attack, so that the compounds and therapeutic agents can be administered on site as soon as possible after a soldier experiences traumatic brain injury. The compounds, therapeutic agents, and methods of the present disclosure can also be used to treat civilians who are victims of violent crimes, including but not limited to, terrorist attacks, and any other mishap that can cause brain damage. Treatment the compositions of the disclosure and therapeutic agents can reduce the incidence of disability presently occurring in the aftermath of traumatic brain injury suffered due to hostilities, including terrorist attacks, other crimes, and accidents.

In some embodiments, compounds of the disclosure and a therapeutic agent can also be used to treat individuals suffering from brain injury due to domestic occurrences, such as traffic accidents (e.g., motor and non-motor vehicle accidents), sports injuries, work related accidents, household accidents, child abuse, domestic violence, and gunshot wounds, including consequential injuries such as disability or epilepsy. In some embodiments, the compounds and therapeutic agent are given prophylactically for contact sports having high incidence of CNS damage.

In some embodiments, the disclosure describes the use of a compound and a therapeutic agent to treat brain damage in a specific region of the brain, such as cerebral lobe (e.g., basal ganglia, cerebellum, or the brainstem) damage, frontal lobe damage, parietal lobe damage, temporal lobe damage, or occipital lobe damage. In some embodiments, the present disclosure describes the use of a compound and a therapeutic agent to treat brain dysfunction according to type: aphasia (language), dysgraphia (writing), dysarthria (speech), apraxia (patterns of sequences of movements), agnosia (identifying things or people), or amnesia (memory). In some embodiments the present disclosure describes the use of a compound and a therapeutic agent to treat spinal cord disorders, peripheral neuropathy and other peripheral nervous system disorders, cranial nerve disorders (e.g., Trigeminal neuralgia), autonomic nervous system disorders (e.g., dysautonomia, Multiple System Atrophy), or seizure disorders (i.e., epilepsy).

In some embodiments, the disclosure describes the use of a compound and a therapeutic agent to treat a movement disorder of the central and peripheral nervous system, such as Essential tremor, Amyotrophic lateral sclerosis, Tourette's syndrome, Multiple Sclerosis, and various types of peripheral neuropathy. In some embodiments, the disclosure describes the use of a compound and a therapeutic agent to treat sleep disorders (e.g., narcolepsy), migraines and other types of headaches, or central neuropathy. In some embodiments, the disclosure describes the use of a compound and a therapeutic agent to treat a neuropsychiatric illness, such as attention deficit hyperactivity disorder, autism, or obsessive compulsive disorder.

In some embodiments, the disclosure describes the use of a compound and a therapeutic agent to treat a neurodegenerative disease. Generally, diseases of the central nervous system are referred to as neurodegenerative, and are characterized by gradually evolving, progressive neuronal death. In some embodiments, the neurodegenerative disease is hereditary with either dominant or recessive inheritance. In some embodiments, the neurodegenerative disease occurs sporadically. The compounds of the disclosure can treat brain damage, for example, brain damage resulting from a mechanical injury, disease, infections, toxic challenges, and excessive use of drugs including recreational, over the counter, or prescription drugs.

In some embodiments, the compounds and therapeutic agents of the disclosure and methods disclosed herein can be used to treat a neurodegenerative disease, for example, Alzheimer Disease, Parkinson Disease, Huntington Disease, Lou Gehrig Disease, Multiple Sclerosis, autoimmune disorders, Pick Disease, diffuse Lewy body Disease, progressive supranuclear palsy (Steel-Richardson syndrome), multisystem degeneration (Shy-Drager syndrome), motor neuron diseases, amyotrophic lateral sclerosis, degenerative ataxias, cortical basal degeneration, ALS-Parkinson-Dementia complex of Guam, subacute sclerosing panencephalitis, synucleinopathies, primary progressive aphasia, striatonigral degeneration, Machado-Joseph disease/spinocerebellar ataxia type 3 and olivopontocerebellar degenerations, Gilles De La Tourette Disease, bulbar and pseudobulbar palsy, spinal and spinobulbar muscular atrophy (Kennedy Disease), primary lateral sclerosis, familial spastic paraplegia, Werdnig-Hoffmann Disease, Kugelberg-Welander Disease, Tay-Sach Disease, Sandhoff Disease, familial spastic disease, Wohlfart-Kugelberg-Welander Disease, spastic paraparesis, progressive multifocal leukoencephalopathy, prion diseases, including Creutzfeldt-Jakob Disease, Gerstmann-Straussler-Scheinker Disease, Kuru, and fatal familial insomnia. In some embodiments, the neurological disease is Parkinson's Disease.

In some embodiments, the methods of the disclosure can treat a brain disorder in a brain of a subject in need thereof, the method comprising intranasally administering to a nose of the subject a dose of N-acetylcysteine (NAC), or a congener thereof, wherein the intranasal administration provides a therapeutically-effective amount of the NAC, or the congener thereof, to the brain from the nose, and wherein the subject is not substantially systemically exposed to the NAC, or the congener thereof, upon the intranasal administration.

In some embodiments, the methods of the disclosure can treat a brain disorder in a brain of a subject in need thereof, the method comprising intranasally administering to a nose of the subject a dose of N-acetylcysteine (NAC), or a congener thereof, wherein the intranasal administration provides a therapeutically-effective amount of the NAC, or the congener thereof, to the brain from the nose, wherein substantially all of the NAC, or the congener thereof, enters the brain without crossing a blood brain barrier of the subject.

In some embodiments, the methods of the disclosure can treat a brain disorder in a brain of a subject in need thereof, the method comprising intranasally administering to a nose of the subject a dose of N-acetylcysteine (NAC), or a congener thereof, wherein the intranasal administration provides a therapeutically-effective amount of the NAC to the brain from the nose, wherein the NAC, or the congener thereof, crosses an olfactory epithelium of the subject after the intranasal administration, and then after crossing the olfactory epithelium, the NAC, or the congener thereof, enters an olfactory nerve of the subject, and then after crossing the olfactory nerve, the NAC, or the congener thereof, enters the brain.

In some embodiments, the methods of the disclosure can treat a brain of a subject in need thereof, the method comprising intranasally administering to a nose of the subject a dose of N-acetylcysteine (NAC), or a congener thereof, wherein the intranasal administration provides a therapeutically-effective amount of the NAC, or the congener thereof, to the brain from the nose, wherein the NAC, or the congener thereof, crosses an olfactory epithelium of the subject after the intranasal administration, and then after crossing the olfactory epithelium, the NAC, or the congener thereof, enters an olfactory nerve of the subject, and then after crossing the olfactory nerve, the NAC, or the congener thereof, enters the cerebral spinal fluid of the subject, and then the NAC, or the congener thereof, enters the brain.

In some embodiments, the methods of the disclosure can treat a brain disorder in a brain of a subject in need thereof, the method comprising intranasally administering to a nose of the subject N-acetylcysteine (NAC), or a congener thereof, wherein the intranasal administration provides a therapeutically-effective amount of the NAC, or the congener thereof, to the brain from the nose, wherein the NAC, or the congener thereof, crosses a respiratory epithelium of the subject after the intranasal administration, and then after crossing the respiratory epithelium, the NAC crosses a trigeminal nerve of the subject, and then after crossing the trigeminal nerve, then NAC enters the brain.

In some embodiments, the methods of the disclosure can treat a brain disorder, wherein the brain disorder is a concussion. In some embodiments, the methods of the disclosure can treat a brain disorder, wherein the brain disorder is post-concussion syndrome. In some embodiments, the methods of the disclosure can treat a brain disorder, wherein the brain disorder is a mild traumatic brain injury. In some embodiments, the methods of the disclosure can treat a brain disorder, wherein the brain disorder is traumatic brain injury. In some embodiments, the methods of the disclosure can treat a brain disorder, wherein the brain disorder is associated with athletic activity. In some embodiments, the methods of the disclosure can treat a brain disorder, wherein the brain disorder is a neurodegenerative disease. In some embodiments, the methods of the disclosure can treat a brain disorder, wherein the brain disorder is dementia. In some embodiments, the methods of the disclosure can treat a brain disorder, wherein the brain disorder is age-related. In some embodiments, the methods of the disclosure can treat a brain disorder, wherein the brain disorder is Parkinson's disease. In some embodiments, the methods of the disclosure can treat a brain disorder, wherein the brain disorder is a stroke.

In some embodiments, the NAC congener is GSH. In some embodiments, substantially all of the dose enters the brain without crossing a blood brain barrier of the subject.

In some embodiments, the NAC, or the congener thereof, crosses an olfactory epithelium of the subject after the intranasal administration, and then after crossing the olfactory epithelium, the NAC, or the congener thereof, enters an olfactory nerve of the subject, and then after crossing the olfactory nerve, the NAC, or the congener thereof, enters the brain. In some embodiments, the NAC, or the congener thereof, crosses an olfactory epithelium of the subject after the intranasal administration, and then after crossing the olfactory epithelium, the NAC, or the congener thereof, enters an olfactory nerve of the subject, and then after crossing the olfactory nerve, the NAC, or the congener thereof, enters the cerebral spinal fluid of the subject, and then the NAC enters the brain. In some embodiments, the NAC, or the congener thereof, wherein the NAC, or the congener thereof, crosses a respiratory epithelium of the subject after the intranasal administration, and then after crossing the respiratory epithelium, the NAC, or the congener thereof, crosses a trigeminal nerve of the subject, and then after crossing the trigeminal nerve, then the NAC, or the congener thereof, enters the brain.

In some embodiments, the therapeutically-effective amount is about 1 mg/kg to about 10 mg/kg. In some embodiments, the therapeutically-effective amount is from about 100 mg to about 400 mg. In some embodiments, the dose is administered using a nasal pump. In some embodiments, the dose is administered using an atomizer. In some embodiments, the dose is administered using a nebulizer. In some embodiments, substantially all of the dose enters a nasal cavity of the subject.

Pharmaceutical Compositions

The present disclosure describes pharmaceutical compositions comprising NAC, NACA, a NAC metabolite, NAC congener, or D-NAC, or a pharmaceutically-acceptable salt thereof that can be administered to a subject to treat brain injury or a CNS condition as described herein. A pharmaceutical composition of the disclosure can be a combination of any pharmaceutical compound described herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts as pharmaceutical compositions by various forms and routes including, for example, intravenous, subcutaneous, intramuscular, oral, parenteral, ophthalmic, subcutaneous, transdermal, nasal, vaginal, and topical administration. A pharmaceutical composition can be administered in a local manner, for example, via injection of the compound directly into an organ, optionally in a depot or sustained release formulation or implant.

A compound of the disclosure can be administered intranasally, and can be formulated into a variety of inhalable compositions, such as solutions, suspensions, vapors, or powders. Intranasal pharmaceutical compositions can contain solubilizers, stabilizers, tonicity enhancing agents, buffers and preservatives.

In practicing the methods of treatment or use provided herein, therapeutically-effective amounts of a compound described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compound used, and other factors. A compound of the disclosure can be used singly or in combination with one or more therapeutic agents as components of mixtures.

Pharmaceutical compositions of the disclosure can be formulated using one or more physiologically-acceptable carriers comprising excipients and auxiliaries, which facilitate processing of the active compounds into preparations that can be used pharmaceutically. A formulation can be modified depending upon the route of administration chosen. Pharmaceutical compositions comprising a compound described herein can be manufactured, for example, by mixing, dissolving, emulsifying, encapsulating, entrapping, or compression processes.

The pharmaceutical compositions of the disclosure can include at least one pharmaceutically-acceptable carrier, diluent, or excipient and compounds described herein as free-base or pharmaceutically-acceptable salt form. Pharmaceutical compositions can contain solubilizers, stabilizers, tonicity enhancing agents, buffers and preservatives.

Methods for the preparation of compositions comprising a compound described herein include formulating a compound with one or more inert, pharmaceutically-acceptable excipients or carriers to form a solid, semi-solid, or liquid composition. Solid compositions include, for example, powders, tablets, dispersible granules, capsules, and cachets. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the disclosure include liquid, powder, gel, nanosuspension, nanoparticle, microgel, aqueous or oily suspensions, emulsion, and any combination thereof.

Non-limiting examples of pharmaceutically-acceptable excipients suitable for use in intranasal formulation of the disclosure include, but are not limited to, mucoadhesive excipients, adsorption enhancers, and preservatives, In some embodiments, the composition comprise mucoadhesive excipient. Mucoadhesive excipients include small molecules, oligomeric molecules or polymers. In some embodiments, mucoadhesive molecules are positively charged to build-up interactions with negatively charged mucins. The mucus consists predominantly of proteins of the mucin family and water. Mucins are bound to the apical surface of epithelial cells. By adhering to such cell bound mucins, these agents prolong the residence at the mucosa and, thus, improve drug uptake. Examples of mucoadhesive compounds include, but are not limited to, chitosan (a copolymer of N-acetyl-D-glucosamine and glucosamine), chitosan derivatives (e.g., N-trimethyl chitosan, carboxylated chitosan), Hypromellose (hydroxypropylmethyl cellulose), carbopol, carboxymethylcellulose, and polyacrylic acid.

In some embodiments, the composition comprise adsorption enhancers. Excipients that improve permeation and absorption are e.g., cyclodextrins, bile salts, laureth-9 sulfate, fusidate derivates, fatty acids, hydrophilic polymers, and surfactants. In some embodiments, methylated β-cyclodextrins are used to enhance the absorption of poorly water soluble, lipophilic drugs since they form inclusion complexes with the drug.

To prolong stability of nasal drug formulations, preservatives can be used. Non-limiting examples of preservatives include lipohilic preservatives such as chlorobutol, hydroxybenzoates, methylhydroxybenzoates, propylhxdroxybenzoates, chlorocresol, edetate, and benzalkonium chloride. In some embodiments, the preservative is a paraben. In some embodiments, the paraben is methylparaben. In some embodiments, the paraben is ethylparaben. In some embodiments, the paraben is propylparaben. In some embodiments, the paraben is butylparaben.

In some embodiments, the formulations are in solid or semi-sold forms, e.g., in the form of hydrogels. Examples of hydrogels include compositions comprising chitosan, carbopol, hydroxypropyl methylcellulose, and/or polyvinyl alcohol. Due to higher viscosity, semisolid formulations can target the olfactory cleft with its mucosa facing either upside-down or upright.

In some embodiments, the compositions are in particle form. In some embodiments, the compositions are in the form of nanoparticles. The use of nanoparticles as drug delivery systems allows controlled and site-specific delivery of therapeutic agents. Nanoparticles are able to protect the drug from biological or chemical degradation and help to evade drug-efflux mechanisms such as P-glycoprotein transporter in the blood-brain barrier, due to encapsulation of the drug. The use of nano- and microparticles for drug delivery brings along some benefits, such as a controlled and sustained drug release or by shielding the drug against environmental influences. Nanocarriers for drug delivery systems include, but are not limited to, polymeric, lipid and inorganic nanoparticles. Biodegradable drug carriers as poly lactic acid (PLA), poly glycolic acid (PGA) and their polymer poly(lactid-co-glycolid) acid (PLGA) are suitable for use in intranasal delivery.

In some embodiments, the compositions are lipid-based compositions. Lipid-based compositions can comprise lipid-based carriers such as mono-, di-, triglycerides, fatty acids and waxes. Nanostructured lipid carriers can be composed of blends of solid and liquid state lipids.

A composition of the disclosure can be, for example, an immediate release form. An immediate release formulation can be formulated to allow a compound to act rapidly. Non-limiting examples of immediate release formulations include readily dissolvable formulations.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for injection can be presented in unit dosage form, for example, in ampoules, or in multi-dose containers with a preservative.

Pharmaceutical compositions provided herein, can be administered in conjunction with other therapies, for example, chemotherapy, radiation, surgery, anti-inflammatory agents, and selected vitamins. The other agents can be administered prior to, after, or concomitantly with the pharmaceutical compositions.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, or gels, for example, in unit dosage form suitable for single administration of a precise dosage.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Compounds can be delivered via liposomal technology. The use of liposomes as drug carriers can increase the therapeutic index of a compound. Liposomes are composed of natural phospholipids, and can contain mixed lipid chains with surfactant properties (e.g., egg phosphatidylethanolamine). A liposome design can employ surface ligands for attaching to unhealthy tissue. Non-limiting examples of liposomes include the multilamellar vesicle (MLV), the small unilamellar vesicle (SUV), and the large unilamellar vesicle (LUV). Liposomal physicochemical properties can be modulated to optimize penetration through biological barriers and retention at the site of administration, and to reduce a likelihood of developing premature degradation and toxicity to non-target tissues.

Optimal liposomal properties depend on the administration route: large-sized liposomes show good retention upon local injection, small-sized liposomes are better suited to achieve passive targeting. PEGylation reduces the uptake of the liposomes by the liver and spleen, and increases the circulation time, resulting in increased localization at the inflamed site due to the enhanced permeability and retention (EPR) effect. Additionally, liposomal surfaces can be modified to achieve selective delivery of the encapsulated drug to specific target cells. Non-limiting examples of targeting ligands include monoclonal antibodies, vitamins, peptides, and polysaccharides specific for receptors concentrated on the surface of cells associated with the disease.

Non-limiting examples of dosage forms suitable for use in the disclosure include liquid, elixir, nanosuspension, aqueous or oily suspensions, drops, syrups, and any combination thereof. Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavoring agents, coating agents, plasticizers, preservatives, suspending agents, emulsifying agents, plant cellulosic material and spheronization agents, and any combination thereof.

A pharmaceutical composition of the disclosure can be in the form of an aqueous solution. In some embodiments, the pharmaceutical composition can comprise from about 5% to about 10%, from about 10% to about 15%, from about 15% to about 20%, from about 20% to about 25%, from about 25% to about 30%, from about 30% to about 35%, from about 35% to about 40%, from about 40% to about 45%, from about 45% to about 50%, from about 50% to about 55%, from about 55% to about 60%, from about 60% to about 65%, from about 65% to about 70%, from about 70% to about 75%, from about 75% to about 80%, from about 80% to about 85%, or from about 85% to about 90% of NAC, NACA, NAC derivative, NAC metabolite, NAC congener, or D-NAC, or a pharmaceutically-acceptable salt thereof in an aqueous solution.

In some embodiments, a pharmaceutical composition of the disclosure can comprise about 5%, about 10%, about 15%, about 20%, about 25%, about 30%, about 35%, about 40%, about 45%, about 50%, about 55%, about 60%, about 65%, about 70%, about 75%, about 80%, about 85%, or about 90% of NAC, NACA, NAC derivative, NAC metabolite, NAC congener, or D-NAC, or a pharmaceutically-acceptable salt thereof in an aqueous solution. In some embodiments, a pharmaceutical composition of the disclosure can comprise about 15%, about 16%, about 17%, about 18%, about 19%, about 20%, about 21%, about 22%, about 23%, about 24%, or about 25% of NAC, NACA, NAC derivative, NAC metabolite, NAC congener, or D-NAC, or a pharmaceutically-acceptable salt thereof in an aqueous solution. In some embodiments, a pharmaceutical composition of the disclosure can comprise about 35%, about 36%, about 37%, about 38%, about 39%, about 40%, about 41%, about 42%, about 43%, about 44%, or about 45% of NAC, NACA, NAC derivative, NAC metabolite, NAC congener, or D-NAC, or a pharmaceutically-acceptable salt thereof in an aqueous solution. In some embodiments, a pharmaceutical composition of the disclosure can comprise about 65%, about 66%, about 67%, about 68%, about 69%, about 70%, about 71%, about 72%, about 73%, about 74%, or about 75% of NAC, NACA, NAC derivative, NAC metabolite, NAC congener, or D-NAC, or a pharmaceutically-acceptable salt thereof in an aqueous solution. In some embodiments, a pharmaceutical composition of the disclosure can comprise about 20% of NAC, NAC, NACA, NAC derivative, NAC metabolite, NAC congener, or D-NAC, or a pharmaceutically-acceptable salt thereof in an aqueous solution. In some embodiments, a pharmaceutical composition of the disclosure can comprise about 25% of NAC, NACA, NAC derivative, NAC metabolite, NAC congener, or D-NAC, or a pharmaceutically-acceptable salt thereof in an aqueous solution. In some embodiments, a pharmaceutical composition of the disclosure can comprise about 30% of NAC, NACA, NAC derivative, NAC metabolite, NAC congener, or D-NAC, or a pharmaceutically-acceptable salt thereof in an aqueous solution.

In some embodiments, a composition of the disclosure can comprise a co-solvent. In some embodiments, the cosolvent is dimethylformamide. In some embodiments, the co-solvent is high purity dimethylformamide. In some embodiments, the cosolvent is dimethylsulfoxide. In some embodiments, a compound of the disclosure can be dissolved in a co-solvent at a concentration of from about 10 mg/mL to about 20 mg/mL, from about 20 mg/mL to about 30 mg/mL, from about 30 mg/mL to about 40 mg/mL, from about 40 mg/mL to about 50 mg/mL, or from about 50 mg/mL to about 60 mg/mL. In some embodiments, a compound of the disclosure can be dissolved in a co-solvent at a concentration of from about 30 mg/mL to about 40 mg/mL. In some embodiments, a compound of the disclosure can be dissolved in a co-solvent at a concentration of from about 40 mg/mL to about 50 mg/mL. In some embodiments, a compound of the disclosure can be dissolved in a co-solvent at a concentration of from about 50 mg/mL to about 60 mg/mL. In some embodiments, a compound of the disclosure can be dissolved in a co-solvent at a concentration of about 10 mg/mL, about 20 mg/mL, about 30 mg/mL, about 40 mg/mL, about 50 mg/mL, about 60 mg/mL. In some embodiments, a compound of the disclosure can be dissolved in a co-solvent at a concentration of about 40 mg/mL. In some embodiments, a compound of the disclosure can be dissolved in a co-solvent at a concentration of about 50 mg/mL. In some embodiments, a compound of the disclosure can be dissolved in a co-solvent at a concentration of about 60 mg/mL Compositions of the disclosure can be packaged as a kit. In some embodiments, a kit includes written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. In some embodiments, the label can be approved by a regulatory agency, for example the U.S. Food and Drug Administration (FDA), the European Medicines Agency (EMA), or other regulatory agencies.

Modes of Administration

A compound of the disclosure can be delivered to the nasal cavity to increase exposure of the compound at the olfactory epithelium or respiratory epithelium. In some embodiments, the compound can be propelled with a specified velocity into the nasal cavity. In some embodiments, the compound can be administered as an intranasal spray. In some embodiments, a compound can be packaged in a pressurized aerosol container with suitable propellants and adjuvants. In some embodiments, the propellant can be a fluid. The fluid can be a liquid, gas, or a combination thereof. In some embodiments, the propellant is a gas (e.g., nitrogen or chloroflourocarbons). In some embodiments, the propellant is pressurized air (e.g. ambient air). In some embodiments, the propellant is a liquid.

In some embodiments, the propellants are hydrocarbon propellants, such as propane, butane, or isobutene. In some embodiments, the propellant is hydrofluoroalkane (HFA), such as HFA, HFA 227, HFA 134a, HFA-FP, or HFA-BP. In some embodiments, aerosol formulations can include other ingredients, such as mucoadhesive agent, adsorption enhancers, co-solvents, stabilizers, surfactants, antioxidants, preservatives, lubricants, and pH adjusters. The aerosol formulations can be administered using a metered dose inhaler. The metered dose inhaler can comprise a pressurized cannister and/or a metering valve to meter the propellant or aerosol formulation upon actuation.

A compound of the disclosure can be administered as a sprayable powder. In some embodiments, a compound can be administered as an inhalable dry powder. In some embodiments, the powder formulation can include pharmaceutically acceptable excipients, such as monosaccharides (e.g., glucose, arabinose), disaccharides (e.g., lactose, saccharose, maltose), oligosaccharides or polysaccharides (e.g., dextrane, polyalcohols (e.g., sorbitol, mannitol, xylitol), salts (e.g., sodium chloride, calcium carbonate), or any combination thereof. In some embodiments, a compound can be administered as a solution, suspension, or a dry powder. In some embodiments, a compound can be administered in a non-pressurized form using a nebulizer or an atomizer.

Delivery of a compound of the disclosure as an intranasal pharmaceutical composition can result in lower systemic drug exposure and fewer side effects. In some embodiments, delivery of the compound results in no systemic drug exposure. In some embodiments, lower systemic drug exposure or no systemic drug exposure can lower the risk of bleeding, gastrointestinal side effects, liver toxicity, fluid retention or edema, neutropenia or leukopenia, anemia, or infection. In some embodiments, lower systemic drug exposure or no systemic drug exposure can lower the risk of gastrointestinal side effects, such as nausea, vomiting, or diarrhea.

A compound of the disclosure can be administered directly to the nasal cavity using an intranasal delivery device. In some embodiments, a compound can be administered intranasally in the form of a vapor or drops. In some embodiments, a compound can be administered using an intranasal delivery device, such as a rhinyle catheter, multi-dose dropper, unit-dose pipette, or vapor inhaler. In some embodiments, a compound can be delivered using a squeeze bottle, multi-dose metered-dose spray pump, single or duo-dose spray pump, or a bidirectional multi-dose spray pump. In some embodiments, a compound can be delivered using an atomizer. In some embodiments, a compound can be delivered using a nebulizer. In some embodiments, the intranasal delivery device can comprise a propellant container, formulation container, or a diffuser. In some embodiments, the intranasal delivery device can comprise a diffuser to diffuse the propellant. In some embodiments, the diffuser can be connected to a formulation container that is configured to hold the formulation. In some embodiments, the diffuser can be connected to a propellant container (e.g., a pressurized propellant container) that is configured to hold the propellant. In some embodiments, the formulation container and the propellant container are the same container. In some embodiments, the formulation container is different from the propellant container. In some embodiments, the propellant can serve as a vehicle to deliver propulsion or thrust to expel the formulation from the formulation container. In some embodiments, the formulation container is connected to a nozzle. In some embodiments, the propulsion or thrust from the propellant is capable of expelling the formulation from the formulation container and the nozzle.

In some embodiments, the diffuser can be porous. In some embodiments, the pores can be homogenous in size and shape. In some embodiments, the pores of the diffuser are heterogeneous in size and shape. In some embodiments, the diffuser is homogenously porous. In some embodiments, the diffuser is heterogeneously porous. In some embodiments, the propellant passes through the pores, but the pores are impervious to the formulation.

In some embodiments, the diffuser is connected to the propellant. In some embodiments, the diffuser can convert a liquid propellant, exiting the propellant container, into a gaseous propellant. In some embodiments, the diffuser can increase a temperature of the resulting gas. In some embodiments, the passage of a gas propellant through the diffuser can increase the temperature of the gas propellant.

Following contact with the diffuser, the diffused propellant can come into contact with the formulation in the formulation container. The diffused propellant and the formulation can come into contact with each other as the propellant propels the formulation in the formulation container through the nozzle. Exiting from the nozzle is the aerosolized formulation, propellant, or a combination thereof. In some embodiments, the nozzle is inserted to a specified length into the subject's nasal cavity. In some embodiments, the nozzle is configured to be a separate inhalation tube that is inserted to a specified length into the subject's nasal cavity from the nostril. In some embodiments, the specified length into the subject's nasal cavity from the nostril can be at least about 0.1 cm, at least about 0.2 cm, at least about 0.3 cm, at least about 0.4 cm, at least about 0.5 cm, at least about 0.6 cm, at least about 0.7 cm, at least about 0.8 cm, at least about 0.9 cm, at least about 1.0 cm, at least about 1.1 cm, at least about 1.2 cm, at least about 1.3 cm, at least about 1.4 cm, at least about 1.5 cm, at least about 1.6 cm, at least about 1.7 cm, at least about 1.8 cm, at least about 1.9 cm, at least about 2.0 cm, at least about 2.1 cm, at least about 2.2 cm, at least about 2.3 cm, at least about 2.4 cm, at least about 2.5 cm, or more. In some embodiments, the specified length into the subject's nasal cavity from the nostril can be about 0.1 cm, about 0.2 cm, about 0.3 cm, about 0.4 cm, about 0.5 cm, about 0.6 cm, about 0.7 cm, about 0.8 cm, about 0.9 cm, about 1.0 cm, about 1.1 cm, about 1.2 cm, about 1.3 cm, about 1.4 cm, about 1.5 cm, about 1.6 cm, about 1.7 cm, about 1.8 cm, about 1.9 cm, about 2.0 cm, about 2.1 cm, about 2.2 cm, about 2.3 cm, about 2.4 cm, or about 2.5 cm. In some embodiments, the specified length into the subject's nasal cavity from the nostril can be at most about 2.5 cm, at most about 2.4 cm, at most about 2.3 cm, at most about 2.2 cm, at most about 2.1 cm, at most about 2.0 cm, at most about 1.9 cm, at most about 1.8 cm, at most about 1.7 cm, at most about 1.6 cm, at most about 1.5 cm, at most about 1.4 cm, at most about 1.3 cm, at most about 1.2 cm, at most about 1.1 cm, at most about 1.0 cm, at most about 0.9 cm, at most about 0.8 cm, at most about 0.7 cm, at most about 0.6 cm, at most about 0.5 cm, at most about 0.4 cm, at most about 0.3 cm, at most about 0.2 cm, at most about 0.1 cm, or less. In some embodiments, the formulation can reach a distance in of at least about 1 cm, at least about 2 cm, at least about 3 cm, at least about 4 cm, at least about 5 cm, at least about 6 cm, at least about 7 cm, at least about 8 cm, at least about 9 cm, at least about 10 cm, or more from the nostril. In some embodiments, the formulation can reach a distance of about 1 cm, about 2 cm, about 3 cm, about 4 cm, about 5 cm, about 6 cm, about 7 cm, about 8 cm, about 9 cm, or about 10 cm from the nostril. In some embodiments, the formulation can reach a distance of at most about 15 cm, at most about 14 cm, at most about 13 cm, at most about 12 cm, at most about 11 cm, at most about 10 cm, at most about 9 cm, at most about 8 cm, at most about 7 cm, at most about 6 cm, at most about 5 cm, at most about 4 cm, at most about 3 cm, at most about 2 cm, at most about 1 cm, or less from the nostril.

In some embodiments, the intranasal delivery device can comprise a nose aiming guide that functions to accommodate the subject's nose. In some embodiments, the nose aiming guide is configured to aim the nozzle at the subject's olfactory region. In some embodiments, the intranasal delivery device comprises a septum aiming guide that is configured to accommodate contacting the subject's septum. In some embodiments, the intranasal delivery device comprises an upper lip aiming guide configured to accommodate the subject's upper lip.

In some embodiments, a compound can be administered intranasally in the form of a powder. In some embodiments, a compound can be delivered using mechanical powder sprayer, breath actuated inhaler, or an insufflator. In some embodiments, a compound can be delivered using a mechanical powder spray device. In some embodiments, a compound can be delivered using a multi-dose powder inhaler, single or duo-dose capsule inhaler, or a nasal inhaler. In some embodiments, a compound can be delivered using an insufflator, or a breath-powered bi-directional delivery system.

In some embodiments, compound of the disclosure can be administered directly to the nasal cavity using an intranasal delivery device. In some embodiments, at least one therapeutically effective dose of the compound is delivered using the intranasal delivery device. In some embodiments, at least one therapeutically effective dose of the compound is delivered to the olfactory epithelium or respiratory epithelium.

In some embodiments, substantially all of the dose enters the nasal cavity of the subject. In some embodiments, at least about 50%, at least about 55%, at least about 60%, at least about 65%, at least about 70%, at least about 75%, at least about 80%, at least about 85%, at least about 90%, at least about 95%, or about 100% of the dose enters the nasal cavity of the subject. In some embodiments, about 50%, about 55%, about 60%, about 65%, about 70%, about 75%, about 80%, about 85%, about 90%, about 95%, or about 100% of the dose enters the nasal cavity of the subject. In some embodiments, at most about 100%, at most about 95%, at most about 90%, at most about 85%, at most about 80%, at most about 75%, at most about 70%, at most about 65%, at most about 60%, at most about 55%, at most about 50%, or less of the dose enters the nasal cavity of the subject.

Dosing

Pharmaceutical compositions described herein can be in unit dosage forms suitable for single administration of precise dosages. In unit dosage form, the formulation is divided into unit doses containing appropriate quantities of one or more compound. The unit dosage can be in the form of a package containing discrete quantities of the formulation. Non-limiting examples are liquids in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi-dose containers with a preservative.

A compound described herein can be administered to a subject in a composition in a range of from, about 1 mg/kg to about 5 mg/kg, about 1 mg/kg to about 10 mg/kg, about 1 mg/kg to about 25 mg/kg, about 10 mg/kg to about 50 mg/kg, about 10 mg/kg to about 75 mg/kg, about 10 mg/kg to about 100 mg/kg, about 50 mg/kg to about 125 mg/kg, about 50 mg/kg to about 150 mg/kg, about 50 mg/kg to about 175 mg/kg, about 50 mg/kg to about 200 mg/kg, about 100 mg/kg to about 225 mg/kg, about 100 mg/kg to about 250 mg/kg, about 100 mg/kg to about 275 mg/kg, about 100 mg/kg to about 300 mg/kg, about 150 mg/kg to about 325 mg/kg, about 150 mg/kg to about 350 mg/kg, about 150 mg/kg to about 375 mg/kg, about 150 mg/kg to about 400 mg/kg, about 250 mg/kg to about 425 mg/kg, about 250 mg/kg to about 450 mg/kg, or about 250 mg/kg to about 500 mg/kg.

In some embodiments, a compound is administered in an amount ranging from about 5 mg/kg to about 50 mg/kg, about 250 mg/kg to about 2000 mg/kg, about 10 mg/kg to about 800 mg/kg, about 50 mg/kg to about 400 mg/kg, about 100 mg/kg to about 300 mg/kg, or about 150 mg/kg to about 200 mg/kg. In some embodiments, a compound described herein can be present in a composition in a range of from about 20 mg/kg to about 400 mg/kg. In some embodiments, a compound described herein can be present in a composition in a range of from about 20 mg/kg to about 240 mg/kg. In some embodiments, a compound described herein can be present in a composition in a range of from about 75 mg/kg to about 150 mg/kg. In some embodiments, a compound described herein can be present in a composition in a range of from about 75 mg/kg to about 150 mg/kg. In some embodiments, a compound described herein can be present in a composition in a range of from about 100 mg/kg to about 150 mg/kg.

In some embodiments, a compound described herein can be present in a composition in an amount of about 75 mg/kg. In some embodiments, a compound described herein can be present in a composition in an amount of about 100 mg/kg. In some embodiments, a compound described herein can be present in a composition in an amount of about 150 mg/kg. In some embodiments, a compound described herein can be present in a composition in an amount of about 200 mg/kg. In some embodiments, a compound described herein can be present in a composition in an amount of about 250 mg/kg. In some embodiments, a compound described herein can be present in a composition in an amount of about 400 mg/kg.

A compound described herein can be present in a composition in a range of from about 1 mg to about 2000 mg, from about 100 mg to about 2000 mg, from about 10 mg to about 2000 mg, from about 5 mg to about 1000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg. In some embodiments, a method of the disclosure administers a therapeutically-effective amount from about 100 mg to about 400 mg.

A compound described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some embodiments, a compound described herein can be present in a composition in an amount of about 100 mg, about 120 mg, about 140 mg, about 160 mg, about 180 mg, about 200 mg, about 220 mg, about 240 mg, about 260 mg, about 280 mg, or about 300 mg. In some embodiments, a compound described herein can be present in a composition in an amount of about 150 mg. In some embodiments, a compound described herein can be present in a composition in an amount of about 170 mg. In some embodiments, a compound described herein can be present in a composition in an amount of about 280 mg. In some embodiments, a compound described herein can be present in a composition in an amount of about 300 mg. In some embodiments, a compound described herein can be present in a composition in an amount of about 350 mg. In some embodiments, a compound described herein can be present in a composition in an amount of about 400 mg.

In some embodiments, a compound of the disclosure can be administered to a subject in a composition in an amount of about 1 mg/kg to about 10 mg/kg. In some embodiments, a compound of the disclosure can be administered to a subject in a composition in an amount of about 1 mg/kg to about 50 mg/kg. In some embodiments, a compound of the disclosure can be administered to a subject in a composition in an amount of about 1 mg/kg to about 75 mg/kg. In some embodiments, a compound of the disclosure can be administered to a subject in a composition in an amount of about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg.

A compound described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some embodiments, a dosage is administered in each nostril in about equal amounts. In some embodiments, about 0.1 mL, about 0.2 mL, about 0.3 mL, about 0.4 mL, about 0.5 mL, about 0.6 mL, about 0.7 mL, about 0.8 mL, about 0.9 mL, or about 1.0 mL of a pharmaceutical composition is administered in each nostril of a subject. In some embodiments, 0.25 mL of a pharmaceutical composition is administered in each nostril per dose. In some embodiments, 0.5 mL of a pharmaceutical composition is administered in each nostril per dose.

In some embodiments, dosing is repeated for each nostril to increase the amount of a compound. In some embodiments, a first dosage of a pharmaceutical composition is about 0.1 mL, about 0.2 mL, about 0.3 mL, about 0.4 mL, about 0.5 mL, about 0.6 mL, about 0.7 mL, about 0.8 mL, about 0.9 mL, or about 1.0 mL per nostril of the subject. In some embodiments, a follow up dosage is the same amount as the first dosage of the pharmaceutical composition is. In some embodiments, a follow up dosage is a different amount as the first dosage of the pharmaceutical composition is. In some embodiments, the follow up dosage is a smaller amount than the first dosage of the pharmaceutical composition is. In some embodiments, the follow up dosage is a greater amount than the first dosage of the pharmaceutical composition is.

In some embodiments, 0.5 mL of a pharmaceutical composition is administered in each nostril per dose, and the dosing is repeated after a period of time to administer a total of 1 mL of a pharmaceutical composition per nostril. In some embodiments, a follow up dose is administered about 5 minutes after administration of the first dose. In some embodiments, 0.5 mL of a pharmaceutical composition is administered in each nostril per dose, and the dosing is repeated twice each after a period of time to administer a total of 1 mL of a pharmaceutical composition per nostril.

Therapeutic agents described herein can be administered before, during, or after the occurrence of a disease or condition, and the timing of administering the composition containing a therapeutic agent can vary. In some embodiments, the compositions can be used as a prophylactic and can be administered continuously to subjects with a propensity to conditions or diseases to lessen a likelihood of the occurrence of the disease or condition. The compositions can be administered to a subject during or as soon as possible after the onset of the symptoms. The administration of the therapeutic agents can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein. A therapeutic agent can be administered as soon as is practicable after the onset of a disease or condition is detected or suspected, and for a length of time necessary for the treatment of the disease, such as, for example, from about 1 month to about 3 months. The length of treatment can vary for each subject.

A compound or pharmaceutical composition of the disclosure can be administered more than one time. In some embodiments, a compound or pharmaceutical composition of the disclosure can be administered once daily. In some embodiments, a compound or pharmaceutical composition of the disclosure can be administered twice daily. In some embodiments, a compound or pharmaceutical composition of the disclosure can be administered three times daily. In some embodiments, a compound or pharmaceutical composition of the disclosure can be administered, and the administration can be repeated at least once. In some embodiments, administration of a compound or a pharmaceutical composition can be repeated once. In some embodiments, administration of a compound or a pharmaceutical composition can be repeated twice. In some embodiments, administration of a compound or a pharmaceutical composition can be repeated three times.

In some embodiments, administration of a compound or a pharmaceutical composition can be repeated after about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, or about 31 days. In some embodiments, administration of a compound or pharmaceutical composition can be repeated after about 7 days. In some embodiments, administration of a compound or pharmaceutical composition can be repeated after about 14 days.

In some embodiments, to administer a therapeutic agent (e.g., NAC, NACA, NAC derivative, NAC metabolite, NAC congener, or D-NAC) is advisable as soon as practical after a subject experiences brain injury, for example traumatic brain injury. In some embodiments, traumatic brain injury and/or secondary brain damage resulting from traumatic brain injury can be treated by administering the compounds and compositions of the disclosure to soldiers the compounds can be administered on site as soon as possible after a soldier experiences traumatic brain injury. In some embodiments, a compound or composition is administered about 1 minute, about 5 minutes, about 10 minutes, about 15 minutes, about 20 minutes, about 25 minutes, about 30 minutes, about 35 minutes, about 40 minutes, about 45 minutes, about 50 minutes, about 55 minutes, or about 1 hour after the onset of brain injury.

Combination Therapy

The compounds or pharmaceutical compositions of the disclosure can be administered with at least one additional therapeutic agent. In some embodiments, the compounds or pharmaceutical compositions of the disclosure can be administered with one additional therapeutic agent. In some embodiments, the compounds or pharmaceutical compositions of the disclosure can be administered with two additional therapeutic agents. In some embodiments, the compounds or pharmaceutical compositions of the disclosure can be administered with three additional therapeutic agents.

Multiple therapeutic agents can be administered in any order or simultaneously. In some embodiments, a compound of the invention is administered in combination with, before, or after treatment with another therapeutic agent. If simultaneously, the multiple therapeutic agents can be provided in a single, unified form, or in multiple forms, for example, as multiple separate pills. The agents can be packed together or separately, in a single package or in a plurality of packages. One or all of the therapeutic agents can be given in multiple doses. If not simultaneous, the timing between the multiple doses can vary to as much as about a month.

In some embodiments, the therapeutic agent is a 5-lipogenase-activating protein (FLAP) inhibitor. In some embodiments, the FLAP inhibitor is MK-866 (L 663536), quiflapon (MK-591), fiboflapon (GSK2190915; AM-803), veliflapon (BAY X 1005; DG-031), AM679, or a pharmaceutically-acceptable salt thereof. In some embodiments, the therapeutic agent is glutathione. In some embodiments, the therapeutic agent is a glutathione-decorated nanoparticle.

In some embodiments, the therapeutic agent is a Cathepsin B inhibitor. In some embodiments, the Cathepsin B inhibitor is antipain dihydrochloride, CA-074, CA-074 methyl ester, Calpain inhibitor I, Calpain inhibitor II, chymostatin, cystatin, E-64, leupeptin trifluoroacetate salt, procathepsin B fragment, Z-Leu-Leu-Leu fluoromethyl ketone. In some embodiments, the Cathepsin B inhibitor is antipain dihydrochloride. In some embodiments, the Cathepsin B inhibitor is CA-074. In some embodiments, the Cathepsin B inhibitor is cystatin. In some embodiments, the Cathepsin B inhibitor is chymostatin.

In some embodiments, the therapeutic agent is a poly (ADP-ribose) polymerase (PARP) inhibitor. In some embodiments, the PARP inhibitor is olaparib, rucaparib, niraparib, talazoparib, veliparib, pamiparib, rucaparib, CEP 9722, E7016, Iniparib, or 3-aminobenzamide. In some embodiments, the PARP inhibitor is olaparib. In some embodiments, the PARP inhibitor is rucaparib. In some embodiments, the PARP inhibitor is niraparib. In some embodiments, the PARP inhibitor istalazoparib.

In some embodiments, the therapeutic agent is probenecid. In some embodiments, the therapeutic agent is phenserine. In some embodiments, the therapeutic agent is a dopaminergic agent.

Therapeutic Effects

Administering NAC, NACA, NAC derivative, NAC metabolite, NAC congener, or D-NAC, or a pharmaceutically-acceptable salt thereof with a therapeutic agent can change the concentration of a NAC neurometabolite in a brain region. In some embodiments, administering NAC, NACA, NAC derivative, NAC metabolite, NAC congener, or D-NAC, or a pharmaceutically-acceptable salt thereof with a therapeutic agent can change the concentration of the therapeutic agent in a brain region. In some embodiments, the brain region is the cerebrum, brainstem, cerebellum, pons, medulla, frontal lobe, parietal lobe, occipital lobe, temporal lobe, left dorsal striatum, occipital cortex, or dorsolateral prefrontal cortex (DLPF). In some embodiments, the brain region is the occipital lobe. In some embodiments, the brain region is the occipital cortex. In some embodiments, the brain region is the cerebellum. In some embodiments, the brain region is the DLPF.

In some embodiments, the administering increases the concentration of a NAC neurometabolite in the brain region. In some embodiments, the administering increases the concentration of a NAC neurometabolite in the brain region by from about 20% to about 300%. In some embodiments, the administering increases the concentration of a NAC neurometabolite in the brain region by from about 5% to about 10%, from about 10% to about 15%, from about 15% to about 20%, from about 20% to about 25%, from about 25% to about 30%, from about 30% to about 35%, from about 35% to about 40%, from about 40% to about 45%, from about 45% to about 50%, from about 50% to about 55%, from about 55% to about 60%, from about 60% to about 65%, from about 65% to about 70%, from about 70% to about 75%, from about 75% to about 80%, from about 80% to about 85%, from about 85% to about 90%, from about 90% to about 95%, or from about 95% to about 100%. In some embodiments, the administering increases the concentration of a NAC neurometabolite in the brain region by from about 100% to about 110%, from about 110% to about 120%, from about 120% to about 140%, from about 140% to about 160%, from about 160% to about 180%, from about 180% to about 200%, from about 200% to about 220%, from about 220% to about 240%, from about 240% to about 260%, from about 260% to about 280%, or from about 280% to about 300%.

In some embodiments, the administering increases the concentration of a NAC neurometabolite in the brain region by about 10%, about 20%, about 30%, about 40%, about 50%, about 60%, about 70%, about 80%, about 90%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, or about 300%. In some embodiments, the administering increases the concentration of a NAC neurometabolite in the brain region by about 20%. In some embodiments, the administering increases the concentration of a NAC neurometabolite in the brain region by about 50%. In some embodiments, the administering increases the concentration of a NAC neurometabolite in the brain region by about 100%. In some embodiments, the administering increases the concentration of a NAC neurometabolite in the brain region by about 150%. In some embodiments, the administering increases the concentration of a NAC neurometabolite in the brain region by about 200%.

In some embodiments, the administering of NAC, NACA, NAC derivative, NAC metabolite, NAC congener, or D-NAC, or a pharmaceutically-acceptable salt thereof modulates the NAC neurometabolite/water ratio in a brain region. In some embodiments, the administering of NAC, NACA, NAC derivative, NAC metabolite, NAC congener, or D-NAC, or a pharmaceutically-acceptable salt thereof modulates the GSH/water ratio in a brain region. In some embodiments, the administering of NAC, NACA, NAC derivative, NAC metabolite, NAC congener, or D-NAC, or a pharmaceutically-acceptable salt thereof increases the GSH/water ratio in a brain region. In some embodiments, the administering of NAC, NACA, NAC derivative, NAC metabolite, NAC congener, or D-NAC, or a pharmaceutically-acceptable salt thereof modulates the NAA/water ratio in a brain region. In some embodiments, the administering of NAC, NACA, NAC derivative, NAC metabolite, NAC congener, or D-NAC, or a pharmaceutically-acceptable salt thereof increases the NAA/water ratio in a brain region.

In some embodiments, the administering of NAC, NACA, NAC derivative, NAC metabolite, NAC congener, or D-NAC, or a pharmaceutically-acceptable salt thereof increases the GSH/water ratio in a region of the brain by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, the administering increases the GSH/water ratio in a region of the brain by about 10%. In some embodiments, the administering increases the GSH/water ratio in a region of the brain by about 20%. In some embodiments, the administering increases the GSH/water ratio in a region of the brain by about 30%. In some embodiments, the administering of NAC, NACA, NAC derivative, NAC metabolite, NAC congener, or D-NAC, or a pharmaceutically-acceptable salt thereof decreases the GSH/water ratio in a region of the brain by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, the administering decreases the GSH/water ratio in a region of the brain by about 10%. In some embodiments, the administering decreases the GSH/water ratio in a region of the brain by about 20%. In some embodiments, the administering decreases the GSH/water ratio in a region of the brain by about 30%.

In some embodiments, the administering of NAC, NACA, NAC derivative, NAC metabolite, NAC congener, or D-NAC, or a pharmaceutically-acceptable salt thereof increases the NAA/water ratio in a region of the brain by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, the administering increases the NAA/water ratio in a region of the brain by about 10%. In some embodiments, the administering increases the NAA/water ratio in a region of the brain by about 20%. In some embodiments, the administering increases the NAA/water ratio in a region of the brain by about 30%. In some embodiments, the administering of NAC, NACA, NAC derivative, NAC metabolite, NAC congener, or D-NAC, or a pharmaceutically-acceptable salt thereof decreases the NAA/water ratio in a region of the brain by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, the administering decreases the NAA/water ratio in a region of the brain by about 10%. In some embodiments, the administering decreases the NAA/water ratio in a region of the brain by about 20%. In some embodiments, the administering decreases the NAA/water ratio in a region of the brain by about 30%.

In some embodiments, the administering of NAC, NACA, NAC derivative, NAC metabolite, NAC congener, or D-NAC, or a pharmaceutically-acceptable salt thereof modulates the NAC neurometabolite/creatine ratio in a brain region. In some embodiments, the administering of NAC, NACA, NAC derivative, NAC metabolite, NAC congener, or D-NAC, or a pharmaceutically-acceptable salt thereof modulates the GSH/creatine ratio in a brain region. In some embodiments, the administering of NAC, NACA, NAC derivative, NAC metabolite, NAC congener, or D-NAC, or a pharmaceutically-acceptable salt thereof increases the GSH/creatine ratio in a brain region. In some embodiments, the administering of NAC, NACA, NAC derivative, NAC metabolite, NAC congener, or D-NAC, or a pharmaceutically-acceptable salt thereof modulates the NAA/creatine ratio in a brain region. In some embodiments, the administering of NAC, NACA, NAC derivative, NAC metabolite, NAC congener, or D-NAC, or a pharmaceutically-acceptable salt thereof increases the NAA/creatine ratio in a brain region.

In some embodiments, the administering of NAC, NACA, NAC derivative, NAC metabolite, NAC congener, or D-NAC, or a pharmaceutically-acceptable salt thereof increases the GSH/creatine ratio in a region of the brain by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, the administering increases the GSH/creatine ratio in a region of the brain by about 10%. In some embodiments, the administering increases the GSH/creatine ratio in a region of the brain by about 20%. In some embodiments, the administering increases the GSH/creatine ratio in a region of the brain by about 30%. In some embodiments, the administering of NAC, NACA, NAC derivative, NAC metabolite, NAC congener, or D-NAC, or a pharmaceutically-acceptable salt thereof decreases the GSH/creatine ratio in a region of the brain by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, the administering decreases the GSH/creatine ratio in a region of the brain by about 10%. In some embodiments, the administering decreases the GSH/creatine ratio in a region of the brain by about 20%. In some embodiments, the administering decreases the GSH/creatine ratio in a region of the brain by about 30%.

In some embodiments, the administering of NAC, NACA, NAC derivative, NAC metabolite, NAC congener, or D-NAC, or a pharmaceutically-acceptable salt thereof increases the NAA/creatine ratio in a region of the brain by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, the administering increases the NAA/creatine ratio in a region of the brain by about 10%. In some embodiments, the administering increases the NAA/creatine ratio in a region of the brain by about 20%. In some embodiments, the administering increases the NAA/creatine ratio in a region of the brain by about 30%. In some embodiments, the administering of NAC, NACA, NAC derivative, NAC metabolite, NAC congener, or D-NAC, or a pharmaceutically-acceptable salt thereof decreases the NAA/creatine ratio in a region of the brain by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, the administering decreases the NAA/creatine ratio in a region of the brain by about 10%. In some embodiments, the administering decreases the NAA/creatine ratio in a region of the brain by about 20%. In some embodiments, the administering decreases the NAA/creatine ratio in a region of the brain by about 30%.

In some embodiments, administering NAC, NACA, NAC derivative, NAC metabolite, NAC congener, or D-NAC, or a pharmaceutically-acceptable salt thereof can increase a GSH/creatine ratio and decrease an NAA/creatine ratio in a region of the brain. In some embodiments, administering NAC, NACA, NAC derivative, NAC metabolite, NAC congener, or D-NAC, or a pharmaceutically-acceptable salt thereof can increase a GSH/creatine ratio by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%; and decrease an NAA/creatine ratio by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% in a region of the brain.

In some embodiments, administering NAC, NACA, NAC derivative, NAC metabolite, NAC congener, or D-NAC, or a pharmaceutically-acceptable salt thereof can increase the delivery of an additional therapeutic agent. In some embodiments, NAC, NACA, NAC derivative, NAC metabolite, NAC congener, or D-NAC, or a pharmaceutically-acceptable salt thereof can act as a promoter to transfer an additional therapeutic agent, wherein the additional therapeutic agent has poor delivery from the nose to the brain.

In some embodiments, administering NAC, NACA, NAC derivative, NAC metabolite, NAC congener, or D-NAC, or a pharmaceutically-acceptable salt thereof with an additional therapeutic agent can increase the delivery of the additional therapeutic agent by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, or at least about 200% as compared to delivery of the additional therapeutic agent alone. In some embodiments, administering NAC, NACA, NAC derivative, NAC metabolite, NAC congener, or D-NAC, or a pharmaceutically-acceptable salt thereof with an additional therapeutic agent can increase the delivery of the additional therapeutic agent by at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, or at least about 10-fold as compared to delivery of the therapeutic agent alone. In some embodiments, administering NAC, NACA, NAC derivative, NAC metabolite, NAC congener, or D-NAC, or a pharmaceutically-acceptable salt thereof with an additional therapeutic agent can increase the delivery of the additional therapeutic agent by at least about 30%. In some embodiments, administering NAC, NACA, NAC derivative, NAC metabolite, NAC congener, or D-NAC, or a pharmaceutically-acceptable salt thereof with an additional therapeutic agent can increase the delivery of the additional therapeutic agent by at least about 50%. In some embodiments, administering NAC, NACA, NAC derivative, NAC metabolite, NAC congener, or D-NAC, or a pharmaceutically-acceptable salt thereof with an additional therapeutic agent can increase the delivery of the additional therapeutic agent by at least about 2-fold. In some embodiments, administering NAC, NACA, NAC derivative, NAC metabolite, NAC congener, or D-NAC, or a pharmaceutically-acceptable salt thereof with an additional therapeutic agent can increase the delivery of the additional therapeutic agent by at least about 5-fold.

In some embodiments, NAC, NACA, NAC derivative, NAC metabolite, NAC congener, or D-NAC, or a pharmaceutically-acceptable salt thereof can be administered with from about 1 mg to about 25 mg, from about 25 mg to about 50 mg, from about 50 mg to about 75 mg, from about 75 mg to about 100 mg, from about 100 mg to about 125 mg, from about 125 mg to about 150 mg, from about 150 mg to about 175 mg, from about 175 mg to about 200 mg, from about 225 mg to about 250 mg, from about 250 mg to about 275 mg, or from about 275 mg to about 300 mg of an additional therapeutic agent to increase the delivery amount of the additional therapeutic agent. In some embodiments, NAC, NACA, NAC derivative, NAC metabolite, NAC congener, or D-NAC, or a pharmaceutically-acceptable salt thereof can be administered with from about 1 mg to about 25 mg of an additional therapeutic agent to increase the delivery amount of the additional therapeutic agent. In some embodiments, NAC, NACA, NAC derivative, NAC metabolite, NAC congener, or D-NAC, or a pharmaceutically-acceptable salt thereof can be administered with from about 100 mg to about 125 mg of an additional therapeutic agent to increase the delivery amount of the additional therapeutic agent.

In some embodiments, NAC, NACA, NAC derivative, NAC metabolite, NAC congener, or D-NAC, or a pharmaceutically-acceptable salt thereof can be administered with about 5 mg, about 10 mg, about 20 mg, about 30 mg, about 40 mg, about 50 mg, about 60 mg, about 70 mg, about 80 mg, about 90 mg, about 100 mg, about 120 mg, about 140 mg, about 160 mg, about 180 mg, about 200 mg, about 220 mg, about 240 mg, about 260 mg, about 280 mg, or about 300 mg of an additional therapeutic agent to increase the delivery amount of the additional therapeutic agent. In some embodiments, NAC, NACA, NAC derivative, NAC metabolite, NAC congener, or D-NAC, or a pharmaceutically-acceptable salt thereof can be administered with about 50 mg of an additional therapeutic agent to increase the delivery amount of the additional therapeutic agent. In some embodiments, NAC, NACA, NAC derivative, NAC metabolite, NAC congener, or D-NAC, or a pharmaceutically-acceptable salt thereof can be administered with about 150 mg of an additional therapeutic agent to increase the delivery amount of the additional therapeutic agent.

In some embodiments, NAC, NACA, NAC derivative, NAC metabolite, NAC congener, or D-NAC, or a pharmaceutically-acceptable salt thereof can be administered with an additional therapeutic agent at a ratio of about 1:10, about 1:9, about 1:8, about 1:7, about 1:6, about 1:5, about 1:4, about 1:3, about 1:2, about 1:1, about 2:1, about 3:1, about 4:1, about 5:1, about 6:1, about 7:1, about 8:1, about 9:1, or about 10:1 to increase the delivery amount of the additional therapeutic agent. In some embodiments, NAC, NACA, NAC derivative, NAC metabolite, NAC congener, or D-NAC, or a pharmaceutically-acceptable salt thereof can be administered with an additional therapeutic agent at a ratio of about 1:10 to increase the delivery amount of the additional therapeutic agent. In some embodiments, NAC, NACA, NAC derivative, NAC metabolite, NAC congener, or D-NAC, or a pharmaceutically-acceptable salt thereof can be administered with an additional therapeutic agent at a ratio of about 1:1 to increase the delivery amount of the additional therapeutic agent. In some embodiments, NAC, NACA, NAC derivative, NAC metabolite, NAC congener, or D-NAC, or a pharmaceutically-acceptable salt thereof can be administered with an additional therapeutic agent at a ratio of about 2:1 to increase the delivery amount of the additional therapeutic agent. In some embodiments, NAC, NACA, NAC derivative, NAC metabolite, NAC congener, or D-NAC, or a pharmaceutically-acceptable salt thereof can be administered with an additional therapeutic agent at a ratio of about 5:1 to increase the delivery amount of the additional therapeutic agent.

In some embodiments, the additional therapeutic agent is an antibacterial agent. In some embodiments, the antibacterial agent is a CNS antibacterial agent, for example betalactam or an aminoglycoside. In some embodiments, the betalactam is a penicillin, cephalosporin, monobactam, or carbapenem. In some embodiments, the aminoglycoside is gentamicin, amikacin, tobramycin, neomycin, or streptomycin. In some embodiments, the additional therapeutic agent is ambroxol. In some embodiments, the additional therapeutic agent is an antibody. In some embodiments, the antibody is aducanumab.

Subjects

A subject disclosed herein can be, for example, an elderly adult, an adult, an adolescent, a pre-adolescent, a child, a toddler, an infant, a neonate, and non-human animals. In some embodiments, a subject is a patient.

EXAMPLES

Example 1: Pharmacokinetic (PK) and Pharmacodynamic (PD) Properties of a Single Dose of IN NAC Various assays were designed and tested assess the feasibility of IN NAC administration for direct nose-to-brain delivery as shown and described for FIGS. 1-4. Assays include studies in healthy participants using $^{1}$H-MRS assessment of change from baseline in NAC-derived metabolic markers in three brain regions (occipital cortex, striatum, and DLPF), following a single dose of 196 mg to 200 mg IN NAC at 1, 3, and 6 hours.

Pharmacokinetics

Figure 2:
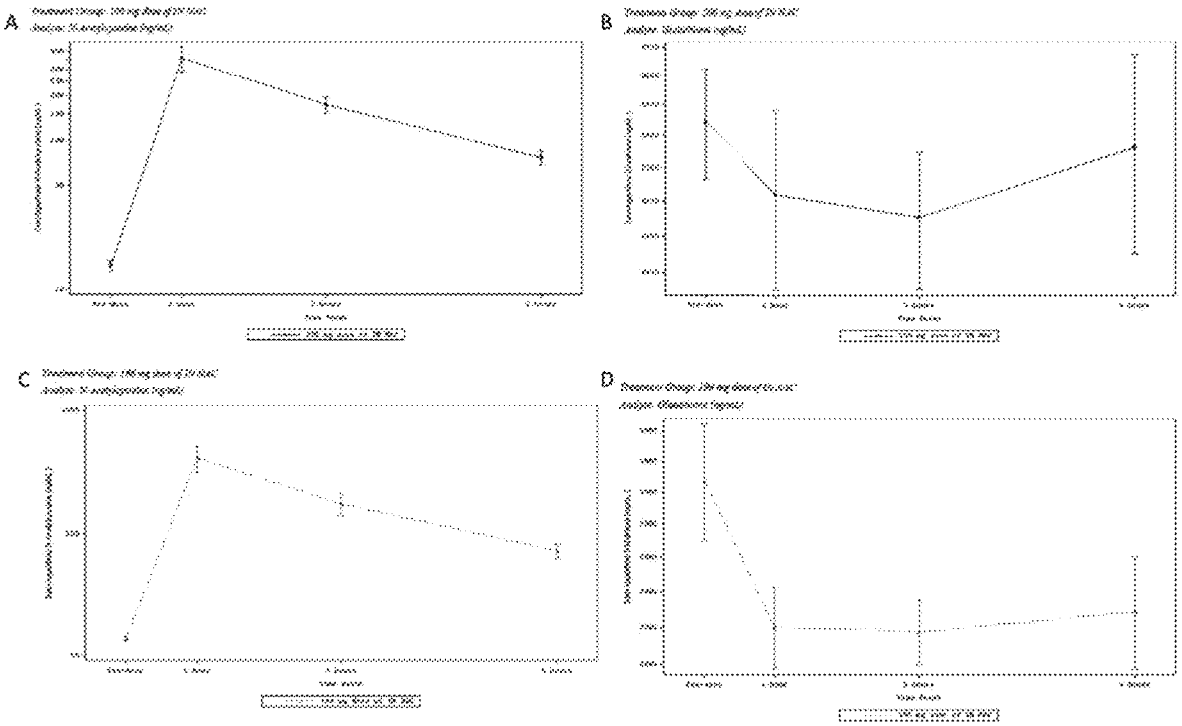
FIG. 2A shows semi-logarithmic NAC mean (±SE) blood PK data over time following 200 mg IN NAC delivered with a Teleflex MAD device.
FIG. 2B shows semi-logarithmic GSH mean (±SE) blood PK data over time following 200 mg IN NAC delivered with a Teleflex MAD device.
FIG. 2C shows semi-logarithmic NAC mean (±SE) blood PK data over time following 196 mg IN NAC delivered with a APTAR 5 mL CPS Syringe.
FIG. 2D shows semi-logarithmic GSH mean (±SE) blood PK data over time following 196 mg IN NAC delivered with a APTAR 5 mL CPS Syringe.

Concentrations of the targeted metabolites were reported for various time points to assess total NAC and GSH concentrations. Mean (±standard error [SE]) of blood PK data were plotted on linear and semi logarithmic scales (FIGS. 1-2).

The mean percentage change from Baseline in NAC for the 200 mg group was 2379.60%, 1117.01%, and 438.17% at 1, 3, and 6 hours post-dose, respectively. For the 196 mg IN NAC group, the mean percentage change from Baseline in NAC was 2881.66%, 1158.20%, and 419.35% at 1, 3, and 6 hours post-dose, respectively. The mean percentage change from Baseline in glutathione for the 200 mg group was −10.00%, −12.20%, and −3.60% at 1, 3, and 6 hours post-dose, respectively. For the 196 mg IN NAC group, the mean percentage change from Baseline in glutathione was −15.60%, −15.90%, −14.30% at 1, 3, and 6 hours post-dose, respectively.

Pharmacodynamics

Figure 3:
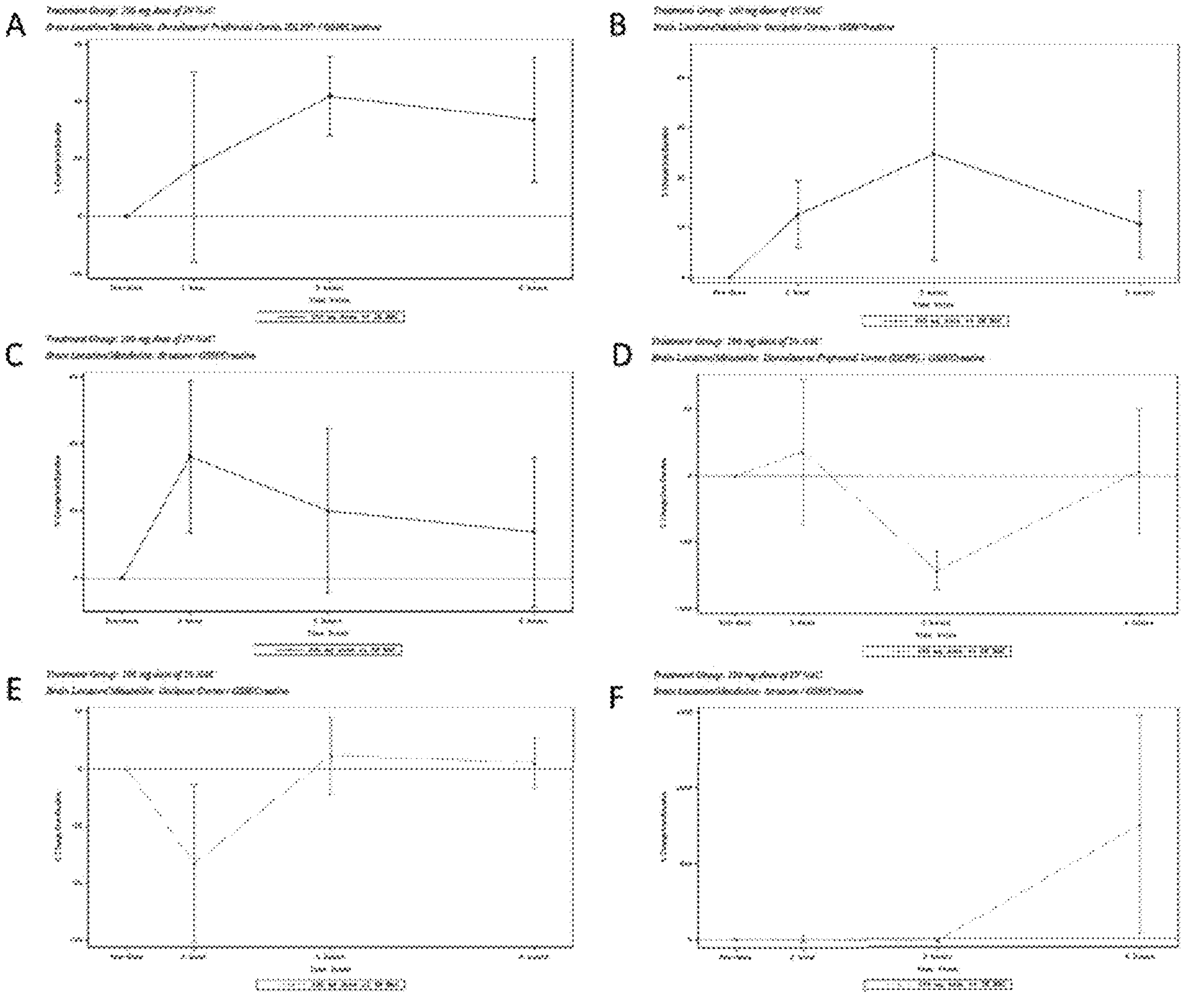
FIG. 3A shows the percentage change from pre-dose baseline (±SE) of GSH/Creatine ratio in the dorsolateral prefrontal cortex (DLPF) region of the brain following 200 mg IN NAC delivered with a Teleflex MAD device.
FIG. 3B shows the percentage change from pre-dose baseline (±SE) of GSH/Creatine ratio in the occipital cortex (OC) region of the brain following 200 mg IN NAC delivered with a Teleflex MAD device.
FIG. 3C shows the percentage change from pre-dose baseline (±SE) of GSH/Creatine ratio in the striatum region of the brain following 200 mg IN NAC delivered with a Teleflex MAD device.
FIG. 3D shows the percentage change from pre-dose baseline (±SE) of GSH/Creatine ratio in the DLPF region of the brain following 196 mg IN NAC delivered with a APTAR 5 mL CPS Syringe.
FIG. 3E shows the percentage change from pre-dose baseline (±SE) of GSH/Creatine ratio in the OC region of the brain following 196 mg IN NAC delivered with a APTAR 5 mL CPS Syringe.
FIG. 3F shows the percentage change from pre-dose baseline (±SE) of GSH/Creatine ratio in the striatum region of the brain following 196 mg IN NAC delivered with a APTAR 5 mL CPS Syringe.
Figure 4:
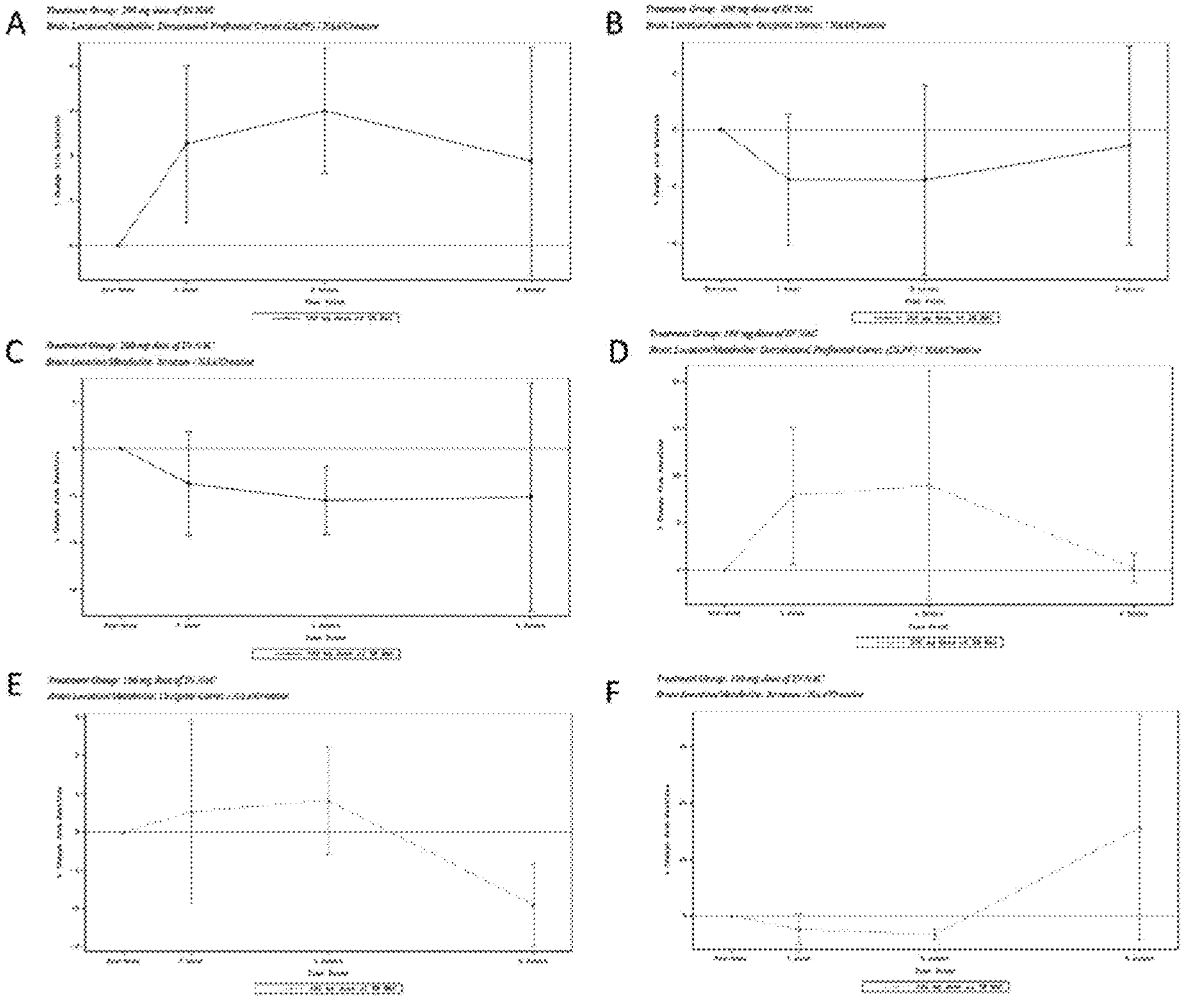
FIG. 4A shows the percentage change from pre-dose baseline (±SE) of NAA/Creatine ratio in the DLPF region of the brain following 200 mg IN NAC delivered with a Teleflex MAD device.
FIG. 4B shows the percentage change from pre-dose baseline (±SE) of NAA/Creatine ratio in the OC region of the brain following 200 mg IN NAC delivered with a Teleflex MAD device.
FIG. 4C shows the percentage change from pre-dose baseline (±SE) of NAA/Creatine ratio in the striatum region of the brain following 200 mg IN NAC delivered with a Teleflex MAD device.
FIG. 4D shows the percentage change from pre-dose baseline (±SE) of NAA/Creatine ratio in the DLPF region of the brain following 196 mg IN NAC delivered with a APTAR 5 mL CPS Syringe.
FIG. 4E shows the percentage change from pre-dose baseline (±SE) of NAA/Creatine ratio in the OC region of the brain following 196 mg IN NAC delivered with a APTAR 5 mL CPS Syringe.
FIG. 4F shows the percentage change from pre-dose baseline (±SE) of NAA/Creatine ratio in the striatum region of the brain following 196 mg IN NAC delivered with a APTAR 5 mL CPS Syringe.

Magnetic resonance (MR) spectra of NAC-derived brain metabolites in three brain regions (occipital cortex, striatum, and DLPF) at baseline and 1, 3, and 6 hours following IN NAC were assessed. Percentage change from Baseline of GSH/Creatine and N-Acetylaspartate (NAA)/Creatine in the three regions by treatment group were plotted (FIGS. 3-4).

In the population receiving 200 mg IN NAC delivered with the Teleflex MAD device (n=6), the regional brain GSH/creatine ratio (in the participants with analysable values in each brain region) increased relative to the pre-dose baselines at 1, 3 and 6 hours post-dose by approximately 36%, 20%, and 14% in striatum (n=4); 17%, 42% and 34% in dorsolateral prefrontal cortex (n=5); and 25%, 49%, and 21% in occipital cortex (n=5) (FIG. 3) as measured by $^{1}$H-MRS. In contrast, in the population receiving 196 mg IN NAC delivered with the APTAR 5 mL CPS Syringe (n=3), the post-dose regional brain GSH/creatine ratios varied inconsistently relative to the pre-dose baseline, increasing by 2% at 1 hour, decreasing by 11% at 3 hours, and showing extreme variability at 6 hours in striatum; decreasing by 17% at 1 hour and increasing by 2% and 1% at 3 and 6 hours in occipital cortex; and increasing by 18% at 1 hour, decreasing 71% at 3 hours, and increasing 4% at 6 hours in the dorsolateral prefrontal cortex. Thus, 200 mg IN NAC delivered with the Teleflex MAD device in 5 participants with analyzable MRS data produced a time- and region-dependent increase in regional brain GSH, reaching peak increases of 36% at 1 hour in the striatum, and reaching a peak increase of 42% and 49% at 3 hours in the dorsolateral prefrontal cortex and occipital cortex, respectively. In contrast, 196 mg of IN NAC delivered with the APTAR 5 mL CPS Syringe failed to produce consistent elevation in regional brain GSH at the 1, 3, and 6 hour post-dose timepoints.

Post-dose changes in the NAA/creatine ratio were minimal (generally within +2.5% of baseline) in striatum and occipital cortex (except for highly variable changes in the 6-hour striatum in the 196 mg cohort). The NAA/creatine ratio tended to increase at 1, 3 and 6 hours post-dose in the dorsolateral prefrontal cortex in both dose groups (4.5%, 6.0% and 3.8% in the 200 mg dose group, and 7.9% and 9.0% in the 196 mg dose group). These results suggest that the initial deacetylation of NAC to L-cysteine and subsequent conversion to GSH may occur more slowly in the dorsolateral prefrontal cortex.

Example 2: Combination Treatment of a Brain Disorder Using N-Acetylcysteine (NAC)

Various assays are designed and tested in a brain disorder model in mice as a function of IN NAC or a pharmaceutically-acceptable salt thereof in combination with various therapeutic agents (e.g., antibiotic, betalactam, an aminoglycoside, ambroxol, an antibody, aducanumab, or farnesol).

The activities of IN NAC and the therapeutic agent are evaluated in combination vs. monotherapy in mouse models. The amount of NAC, NAA, and/or GSH are quantified in one or more regions of the brain.

Administering a combination of IN NAC and the therapeutic agent delivers the therapeutic agent to brain tissue of the mouse in an amount that is at least about 20% greater than an amount of the therapeutic agent delivered to the brain tissue of the subject when administered without the dose of IN NAC.

Example 3: Combination Treatment of a Brain Disorder Using N-Acetylcysteine (NAC)

A subject with a brain disorder is treated with IN NAC or a pharmaceutically-acceptable salt thereof in combination with various therapeutic agents (e.g., antibiotic, betalactam, an aminoglycoside, ambroxol, an antibody, aducanumab, or farnesol).

The amount of NAC, NAA, and/or GSH are quantified in one or more regions of the brain. Administering a combination of IN NAC and the therapeutic agent delivers the therapeutic agent to brain tissue of the subject in an amount that is at least about 20% greater than an amount of the therapeutic agent delivered to the brain tissue of the subject when administered without the dose of IN NAC.

The invention claimed is:

1. A method comprising administering to a subject in need thereof:

a) a dose of a compound, wherein the compound is N-acetylcysteine (NAC) or a pharmaceutically-acceptable salt thereof or glutathione (GSH); and b) a therapeutically-effective amount of a therapeutic agent, wherein the administering delivers the therapeutic agent to a brain tissue of the subject in an amount that is at least about 20% greater than an amount of the therapeutic agent delivered to the brain tissue of the subject when administered without the dose of the compound.

2. The method of claim 1, wherein the administering of the compound is intranasal.

3. The method of claim 1, wherein the subject is human.

4. The method of claim 1, wherein substantially all of the dose of the compound enters the brain without crossing a blood brain barrier of the subject.

5. The method of claim 1, wherein the dose of the compound is a therapeutically-effective amount.

6. The method of claim 1, wherein the dose of the compound is from about 1 mg/kg to about 10 mg/kg.

7. The method of claim 1, wherein the dose of the compound is from about 100 mg to about 400 mg.

8. The method of claim 1, wherein the dose of the compound is administered using a nasal pump.

9. The method of claim 1, wherein the dose of the compound is administered using an atomizer.

10. The method of claim 1, wherein the dose of the compound is administered using a nebulizer.

11. The method of claim 1, wherein substantially all of the dose of the compound enters the nasal cavity of the subject.

12. The method of claim 1, wherein the compound and the therapeutic agent are in a unit dose form.

13. The method of claim 1, wherein the therapeutic agent is an antibiotic.

14. The method of claim 1, wherein the therapeutic agent is a betalactam.

15. The method of claim 1, wherein the therapeutic agent is an aminoglycosi de.

16. The method of claim 1, wherein the therapeutic agent is ambroxol.

17. The method of claim 1, wherein the therapeutic agent is an antibody.

18. The method of claim 1, wherein the therapeutic agent is aducanumab.

19. The method of claim 1, wherein the therapeutic agent is farnesol.

20. The method of claim 1, wherein the administering delivers the therapeutically-effective amount of the therapeutic agent to the brain tissue of the subject in an amount that is at least about 30% greater than an amount of the therapeutic agent delivered to the brain tissue of the subject when administered without the dose of the compound.

21. The method of claim 1, wherein the administering delivers the therapeutically-effective amount of the therapeutic agent to the brain tissue of the subject in an amount that is at least about 50% greater than an amount of the therapeutic agent delivered to the brain tissue of the subject when administered without the dose of the compound.

22. A method of treating a brain disorder in a subject in need thereof, the method comprising intranasally administering to a nose of the subject:

a) a dose of a compound, wherein the compound is N-acetylcysteine (NAC) or a pharmaceutically-acceptable salt thereof or glutathione (GSH); and b) a therapeutically-effective amount of a therapeutic agent, wherein the brain disorder is any of a traumatic brain injury, a mild traumatic brain injury, a concussion, post-concussion syndrome, a stroke, a neurodegenerative disease, dementia, Parkinson's disease, or an age-related disorder.

23. The method of claim 22, wherein the dose of the compound is a therapeutically-effective amount.

24. The method of claim 22, wherein the brain disorder is a concussion.

25. The method of claim 22, wherein the brain disorder is a mild traumatic brain injury.

26. The method of claim 22, wherein the brain disorder is a traumatic brain injury.

27. The method of claim 22, wherein the brain disorder is associated with athletic activity.

28. The method of claim 22, wherein the brain disorder is a neurodegenerative disease.

29. The method of claim 22, wherein the brain disorder is dementia.

30. The method of claim 22, wherein the brain disorder is age-related.

31. The method of claim 22, wherein the brain disorder is a stroke.

32. The method of claim 22, wherein substantially all of the dose of the compound enters the brain without crossing a blood brain barrier of the subject.

33. The method of claim 22, wherein the therapeutically-effective amount of the compound is about 1 mg/kg to about 10 mg/kg.

34. The method of claim 22, wherein the therapeutically-effective amount of the compound is from about 100 mg to about 400 mg.

35. The method of claim 22, wherein the dose of the compound is administered using a nasal pump.

36. The method of claim 22, wherein the dose of the compound is administered using an atomizer.

37. The method of claim 22, wherein the dose of the compound is administered using a nebulizer.

38. The method of claim 22, wherein substantially all of the dose of the compound enters a nasal cavity of the subject.

39. The method of claim 22, wherein the compound and the therapeutic agent are in a unit dose form.

40. The method of claim 22, wherein the administering delivers the therapeutically-effective amount of the therapeutic agent to a brain tissue of the subject in an amount that is at least about 20% greater than an amount of the therapeutic agent delivered to the brain tissue when administered without the dose of the compound.

41. The method of claim 22, wherein the administering delivers the therapeutically-effective amount of the therapeutic agent to a brain tissue of the subject in an amount that is at least about 30% greater than an amount of the therapeutic agent delivered to the brain tissue of the subject when administered without the dose of the compound.

42. The method of claim 22, wherein the administering delivers the therapeutically-effective amount of the therapeutic agent to a brain tissue of the subject in an amount that is at least about 50% greater than an amount of the therapeutic agent delivered to the brain tissue of the subject when administered without the dose of the compound.

43. The method of claim 22, wherein the brain disorder is Parkinson's disease.

* * * * *